United States Patent [19]
Maruta et al.

[11] Patent Number: 5,591,611
[45] Date of Patent: Jan. 7, 1997

[54] TREHALOSE-RELEASING ENZYME, AND ITS PREPARATION AND USES

[75] Inventors: Kazuhiko Maruta, Okayama; Michio Kubota, Osaka; Toshiyuki Sugimoto; Toshio Miyake, both of Okayama, all of Japan

[73] Assignee: Kabushiki Kaisha Hayashibara Seibutsu Kagaku Kenkyujo, Okayama, Japan

[21] Appl. No.: 464,522

[22] Filed: Jun. 5, 1995

Related U.S. Application Data

[62] Division of Ser. No. 253,171, Jun. 2, 1994, Pat. No. 5,472,863.

[30] Foreign Application Priority Data

Jun. 3, 1993 [JP] Japan ..................... 5-156338
Dec. 9, 1993 [JP] Japan ..................... 5-340343
Mar. 28, 1994 [JP] Japan ..................... 6-79291

[51] Int. Cl.$^6$ .............. C12P 19/12; C12N 9/26; C12N 9/14; C12N 9/10
[52] U.S. Cl. ............... 435/100; 435/72; 536/123.13; 514/777; 514/778
[58] Field of Search .................. 514/777, 778; 536/123.13; 435/100, 72

[56] References Cited

U.S. PATENT DOCUMENTS

| | | | |
|---|---|---|---|
| 4,762,857 | 8/1988 | Bollin, Jr. et al. | 514/777 |
| 5,169,767 | 12/1992 | Matsuura et al. | 435/100 |
| 5,218,096 | 6/1993 | Shibuya et al. | 536/41 |

FOREIGN PATENT DOCUMENTS

| | | |
|---|---|---|
| 0483755 | 5/1992 | European Pat. Off. . |
| 0555540 | 8/1993 | European Pat. Off. . |
| 2671099 | 3/1992 | France . |

*Primary Examiner*—Michael G. Wityshyn
*Assistant Examiner*—Francisco C. Prats
*Attorney, Agent, or Firm*—Browdy and Neimark

[57] ABSTRACT

Disclosed is a trehalose-releasing enzyme which specifically hydrolyzes the linkage between a trehalose moiety and the remaining glycosyl moiety in a non-reducing saccharide having a trehalose structure as an end unit and having a degree of glucose polymerization of 3 or higher. The molecular weight of the enzyme is about 57,000 to 68,000 daltons on SDS-PAGE, and the isoelectric point is about 3.3 to 4.6 on isoelectrophoresis. The enzyme is useful in an industrial-scale preparation of trehalose, and the trehalose prepared therewith can be readily incorporated into food products, as well as cosmetic- and pharmaceutical-compositions.

21 Claims, 5 Drawing Sheets

5,591,611

TREHALOSE-RELEASING ENZYME, AND ITS PREPARATION AND USES

This is a division of parent application Ser. No. 08/253,171 filed Jun. 2, 1994, now U.S. Pat. No. 5,472,863.

BACKGROUND OF THE INVENTION

1. Field of the Invention

The present invention relates to a trehalose-releasing enzyme, and its preparation and uses, more particularly, to a novel trehalose-releasing enzyme which specifically hydrolyzes the linkage between a trehalose moiety and the remaining glycosyl moiety in non-reducing saccharides having a trehalose structure as an end unit and having a glucose polymerization degree of 3 or higher, and to the preparation of the enzyme. The present invention further relates to microorganisms capable of form the enzyme, trehalose obtained by us the enzyme, and compositions contain the trehalose.

2. Description of the Prior Art

Trehalose or α, α-trehalose has been known as a non-reducing saccharide consisting of Glucose units. As is described in *Advances in Carbohydrate Chemistry*, Vol. 18, pp. 201–225 (1963), published by Academic Press, USA, and *Applied and Environmental Microbiology*, Vol. 56, pp. 3,213–3,215 (1990), trehalose widely exists in microorganisms, mushrooms, insects, etc., though the content is relatively low. Trehalose is a non-reducing saccharide, so that it neither reacts with substances containing amino groups such as amino acids and proteins, induces the amino-carbonyl reaction, nor deteriorates amino acid-containing substances. Thus, trehalose would be used without a fear of causing an unsatisfactory browning and deterioration. Because of these, the establishment of the industrial-scale preparation of trehalose has been in great demand.

Conventional preparations of trehalose are, for example, those which are disclosed in Japanese Patent Laid-Open No. 154,485/75 wherein microorganisms are utilized, and reported in Japanese Patent Laid-Open No. 216,695/83 wherein maltose is converted into trehalose by using maltose- and trehalose-phosphorylases in combination. The former, however, is not suitable for the industrial-scale preparation because the content of trehalose present in microorganisms used as a starting material is usually lower than 15 w/w % (the wording "w/w %" is abbreviated as "%" in the specification, unless otherwise specified), on a dry solid basis (d.s.b.), and the extraction and purification steps are complicated. The latter has the following demerits: Since trehalose is formed via glucose-1-phosphate, the concentration of maltose as a substrate could not be set to a satisfactorily high-level; (ii) the enzymatic reaction systems of the phosphorylases are reversible reactions, and their yields of the objective trehalose are relatively low; and (iii) it is substantially difficult to retain their reaction systems stably and to continue their enzymatic reactions smoothly. Thus, these conventional preparations have not been actually used as an industrial-scale preparation.

As regards the preparation of trehalose, it is reported in the column titled *"Oligosaccharides"* in the chapter titled *"Current Status of Starch Application Development and Related Problems"* in *"Food Chemicals"*, No. 88, pp.67–72 (August, 1992) that "In spite of a wide applicability of trehalose, the enzymatic preparation via a direct saccharide-transfer reaction or a hydrolytic reaction has been reported to be scientifically almost impossible in this field." Thus, the preparation of trehalose by an enzymatic reaction using starch as a material has ben deemed to be scientifically very difficult.

It is known that partial starch hydrolysates, prepared from a material starch such as liquefied starch, dextrins and maltooligosaccharides, exhibit a reducing power owing to their reducing end groups. The reducing power of these reducing partial starch hydrolysates is generally expressed by "Dextrose Equivalent (DE) value", based on a dry weight. It is known that among reducing partial starch hydrolysates those with a relatively-high DE value generally have a relatively-low molecular weight and viscosity, as well as a relatively-high level of sweetness and reactivity, and readily react with substances having amino groups such as amino acids and proteins to cause an unsatisfactory browning, smell and deterioration of their quality.

Since the properties of reducing partial starch hydrolysates are varied dependently on their DE values, the relationship between reducing partial starch hydrolysates and their DE values is significant. It has been even believed impossible to break away the relationship in this field.

The present inventors, however, did change this common sense and succeeded to establish a preparation of trehalose as disclosed in Japanese Patent Application No. 362,131/92 wherein trehalose is directly produced from non-reducing partial starch hydrolysates by allowing glucoamylase together with a non-reducing saccharide-forming enzyme capable of forming non-reducing saccharides, having a trehalose structure as an end unit and having a degree of glucose polymerization of 3 or higher, to act on reducing partial starch hydrolysates having a degree of glucose polymerization of 3 or higher, prepared from a material starch. Although the preparation of trehalose yields trehalose from non-reducing partial starch hydrolysates in a yield of about 30% and can be feasible as an industrial-scale preparation, there still remains some fear of resulting in a high production cost in view of the trehalose yield. Therefore, the establishment of a novel preparation of trehalose, which forms trehalose from non-reducing partial starch hydrolysates in an increased yield, is in great demand.

SUMMARY OF THE INVENTION

The object of the present invention is to provide a novel preparation of trehalose in a relatively-high yield from relatively-low cost and stably suppliable starch.

In order to attain the aforementioned object, the present inventors have extensively screened microorganisms capable of producing a novel enzyme which releases trehalose from non-reducing partial starch hydrolysates having a trehalose structure as an end unit and having a degree of glucose polymerization of 3 or higher. As a result, we found that a non-reducing saccharide-forming microorganism of the genus Rhizobium, i.e. Rhizobium sp. M-11, isolated from a solid, as disclosed in Japanese Patent Application No. 362,131/92; and a non-reducing saccharide-forming microorganism of the genus Arthrobacter, i.e. Arthrobacter sp. Q36, isolated from a soil, as disclosed in Japanese Patent Application No. 265,416/93, produces a novel trehalose-releasing enzyme. We also found that the novel trehalose-releasing enzyme facilitates a reaction to form trehalose in a satisfactorily-high yield when used in combination with a non-reducing saccharide-forming enzyme, and that trehalose is readily prepared by allowing the novel trehalose-releasing enzyme and a non-reducing saccharide-forming enzyme to act on reducing partial starch hydrolysates, and recovering a reaction mixture containing a relatively-high purity trehalose. We extensively screened microorganisms which produce such a trehalose-releasing enzyme from among known microorganisms. As a result, we found that microorganisms of the genera Brevibacterium and Micrococcus produce a trehalose-releasing enzyme which forms trehalose from non-reducing saccharides having a trehalose structure as an end unit and having a degree of glucose polymerization of 3 or higher similarly as the trehalose-releasing enzymes derived from microorganisms of the genera Rhizobium and Arthrobacter, and accomplished this invention. We also established compositions such as food products, cosmetics and pharmaceuticals containing the trehalose prepared by the aforesaid preparation, and accomplished this invention.

BRIEF EXPLANATION OF THE ACCOMPANYING DRAWINGS

DETAILED DESCRIPTION OF THE INVENTION

Figure 1:
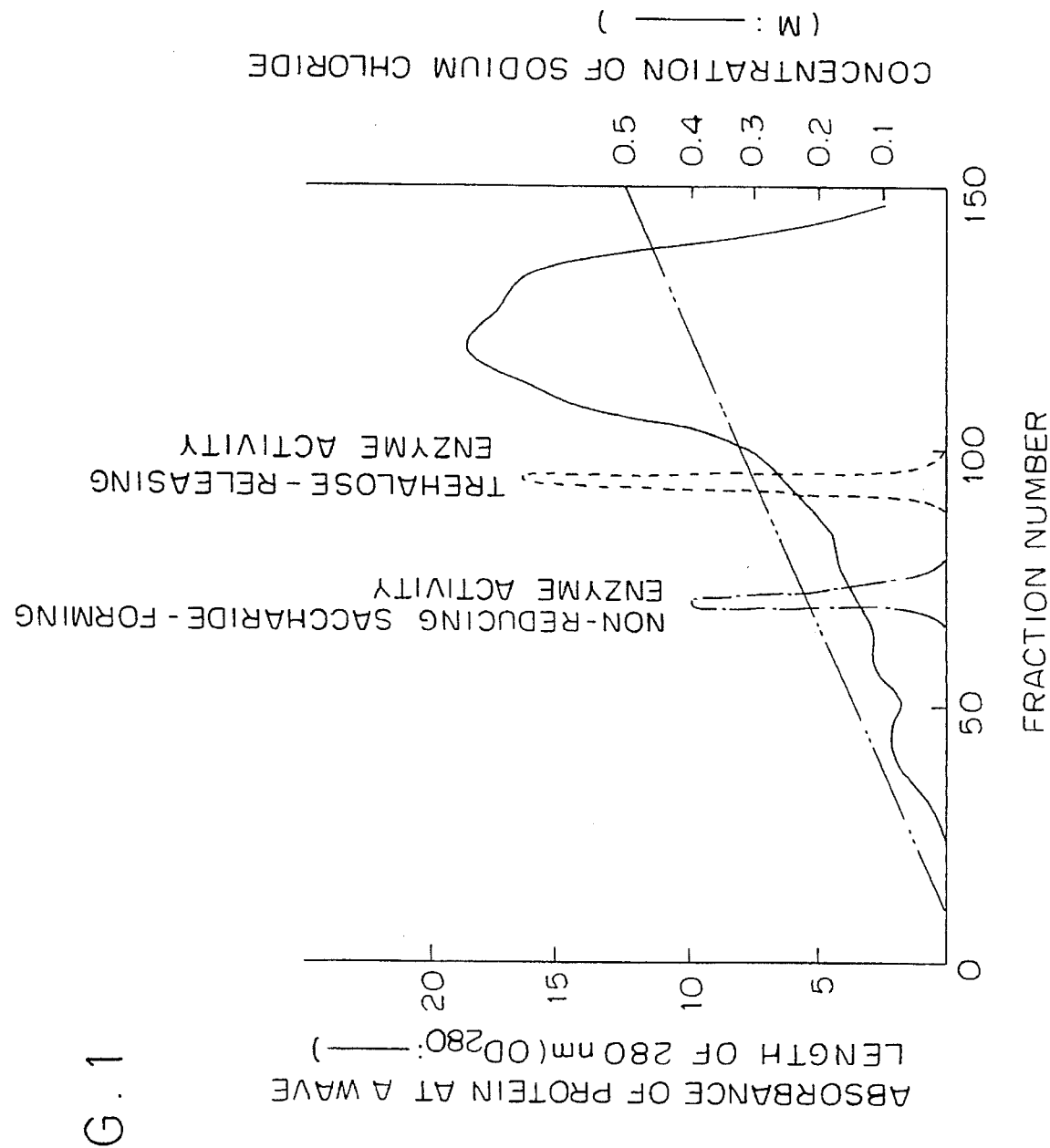
FIG. 1 shows elution patterns of the present trehalose-releasing enzyme and a non-reducing saccharide-forming enzyme eluted from a column packed with a gel of "DEAE-Toyopearl®".

The identification test of a microorganism of the genus Rhizobium, i.e. "Rhizobium sp. M-11" according to the present invention gave the following results. The test was conducted in accordance with the method as described in "Biseibutsu-no-Bunrui-to-Dotei" (Classification and Identification of Microorganisms), edited by Takeji Hasegawa, published by Japan Scientific Societies Press, Tokyo, Japan (1985):

A. Morphology
  Characteristics of cells when incubated at 27° C. in nutrient agar
  Usually existing in a rod form of 0.6–0.8×1.0–1.5 μm;
  Existing single but uncommonly existing in a serially coupled- or a linked-form;
  Exhibiting no polymorphism;
  Possessing motility, asporogenicity and flagellum;
  Non-acid fast;
  Gram stain: Negative;
  Capsule: Negative;
  Metachromatic granule: Positive; and
  Accumulating poly-β-hydroxy butyrate.

B. Cultural property
  (1) Characteristics of colony formed when incubated at 27° C. in nutrient agar plate
    Shape : Circular colony having a diameter of about 1.5 mm after 24-hours incubation;
    Rim: Entire;
    Projection: Plain or hemispherical shape;
    Gloss: Positive;
    Surface: Smooth;
    Color: Creamy and semitransparent colony which forms no pink pigment;
  (2) Characteristics of colony formed when incubated at 27° C. in agar plate with dextrose and trypton
    Creamy and semitransparent colony with mucoid;
  (3) Characteristics of colony formed when incubated at 27° C. in agar plate with yeast extract and mannitol
    Shape : Circular colony having a diameter of about 3 mm after 5-days incubation;
    Color : Creamy and semitransparent colony with mucoid;
  (4) Characteristics of colony formed when incubated at 27° C. in agar plate with yeast extract, mannitol and congo red Exhibiting neither a pale pink nor a substantial absorption of congo red;
  (5) Growing at 27° C. in agar plate with yeast extract, mannitol and 2% NaCl;
  (6) Characteristics of colony formed when incubated at 27° C. in slant nutrient agar
    Growth : Satisfactory;
    Shape : Thread-like; and
  (7) Not liquefying gelatin when stab-cultured at 27° C. in nutrient gelatin.

C. Physiological properties
  (1) Reduction of nitrate: Positive;
  (2) Denitrification reaction: Negative;
  (3) Methyl red test: Negative;
  (4) VP-test: Negative;
  (5) Formation of indole: Negative;
  (6) Formation of hydrogen sulfide: Positive;
  (7) Hydrolysis of starch: Negative;
  (8) Utilization of citric acid: Positive;
  (9) Utilization of inorganic nitrogen source:
    Utilizing ammonium salts and nitrates;
  (10) Formation of pigment: Non;
  (11) Urease: Positive;
  (12) Oxidase: Negative;
  (13) Catalase: Positive;
  (14) Growth conditions: Growing at a pH in the range of 5.5–90 and a temperature in the range of 4°–35° C.;
  (15) Oxygen requirements: Aerobic;
  (16) Utilization of carbon source and acid formation

| Carbon source | Utilization | Acid formation |
|---|---|---|
| D-Glucose | + | + |
| D-Galactose | + | + |
| D-Fructose | + | + |
| L-Arabinose | + | + |
| D-Xylose | + | + |

-continued

| Carbon source | Utilization | Acid formation |
| --- | --- | --- |
| L-Rhamnose | + | + |
| Maltose | + | − |
| Sucrose | + | + |
| Lactose | + | − |
| Trehalose | + | − |
| Raffinose | + | + |
| Mannitol | + | − |
| Dextrin | + | − |
| Dulcitol | + | − |

(17) Decarboxylase test on amino acid
　　Negative against L-lysine, L-arginine and L-ornithine;
(18) Utilization of amino acid
　　Utilizing sodium L-glutamate, sodium L-asparate, L-histidine and L-proline;
(19) DNase: Negative;
(20) Formation of 3-ketolactose: Negative; and
(21) Mol% guanine (G) plus cytosine (C) of DNA: 61%.

The bacteriological properties were compared with those of known microorganisms with reference to *Bergeh's Manual of Systematic Bacteriology*, 1st edition (1984). As a result, it was revealed that the microorganism was identified as a microorganism of the genus Rhizobium. The microorganism is similar to those of the species *Rhizobium meliloti*, but it is distinguishable from them in that it utilizes maltose, lactose and mannitol but forms no acid, and in that it produces both an enzyme, which forms non-reducing saccharides having a trehalose structure when allowed to act on reducing partial starch hydrolysates, and a novel trehalose-releasing enzyme which specifically hydrolyzes the linkage between a trehalose moiety and the remaining glycosyl moiety in a non-reducing saccharide to lease the trehalose moiety. No publication has reported such a microorganism having these properties.

The microorganism had been named "Rhizobium sp. M-11" by the present inventors and deposited on Dec. 24, 1992, in Fermentation Research Institute, Agency of Industrial Science and Technology, Ibaraki, Japan. The deposition of the microorganism was accepted on the same day and has been maintained by the institute under the accession number of FERM BP-4130.

In addition to the above-identified microorganism, other strains of the genus Rhizobium and their mutants can be suitably used in the invention as long as they produce the present trehalose-releasing enzyme.

The identification test of a microorganism of the genus Arthrobacter, i.e. Arthrobacter sp. Q36 according to the present invention gave the following results. The test was conducted in accordance with the method as described in "Biseibutsu-no-Bunrui-to-Dotei" (Classification and Identification of Microorganisms), edited by Takeji Hasegawa, published by Japan Scientific Societies Press, Tokyo, Japan (1985). The results were as follows:

A. Morphology
　(1) Characteristics of cells when incubated at 27 in nutrient agar
　　Usually exhibiting a rod form of 0.5–0.7×0.8–1.6 μm; Existing single;
　　Exhibiting polymorphism;
　　Possessing no motility, flagellum and asporogenicity;
　　Non-acid fast;
　　Gram stain: Positive;
　　Capsule: Negative; and
　(2) Characteristics of cells when incubated at 27° C. in EYG agar.
　　Exhibiting a rod-coccus cycle.
B. Cultural property
　(1) Characteristics of colony formed when incubated at 27° C. in nutrient agar plate
　　Shape : Circular colony having a diameter of about 2–2.5 mm after 3-days incubation;
　　Rim: Entire;
　　Projection: Hemispherical shape;
　　Gloss: Moist gloss;
　　Surface: Smooth;
　　Color: Semitransparent and white or pale yellow;
　(2) Characteristics of cells when slant-cultured at 27° C. in nutrient agar plate
　　Growth rate: Satisfactory; and
　　Shape: Thread-like;
　(3) Characteristics of cells when slant-cultured at 27° C. in agar plate containing yeast extract and peptone
　　Growth rate: Satisfactory;
　　Shape : Thread-like; and
　(4) Characteristics of cells when stub-cultured at 27° C. in bouillon and gelatin Liquefying bouillon and gelatin.
C. Physiological properties
　(1) Reduction of nitrate: Positive;
　(2) Denitrification reaction: Negative;
　(3) Methyl red test: Negative;
　(4) VP-test: Positive;
　(5) Formation of indole: Negative;
　(6) Formation of hydrogen sulfide: Positive;
　(7) Hydrolysis of starch: Negative;
　(8) Hydrolysis of cellulose: Negative;
　(9) Utilization of citric acid: Positive;
　(10) Utilization of inorganic nitrogen source
　　Utilizing ammonium salts and nitrates;
　(11) Formation of pigment: Negative;
　(12) Urease: Positive;
　(13) Oxidase: Negative;
　(14) Catalase: Positive;
　(15) Growth conditions: Growing at a pH in the range of 5–10 and a temperature in the range of 4°–37° C.;
　(16) Oxygen requirements: Aerobic;
　(17) Utilization of carbon source and acid formation

| Carbon source | Utilization | Acid formation |
| --- | --- | --- |
| D-Glucose | + | − |
| D-Galactose | + | − |
| D-Fructose | + | − |
| L-Arabinose | + | − |
| D-Xylose | + | − |
| L-Rhamnose | + | − |
| Maltose | + | − |
| Sucrose | + | − |
| Lactose | + | − |
| Raffinose | + | − |
| Mannitol | + | − |
| Dextrin | + | − |
| Dulcitol | + | − |

(18) Utilization of amino acid
　　Utilizing sodium L-glutamate, sodium L-asparate, L-histidine and L-proline;
(19) DNase: Positive;
(20) Formation of 3-ketolactose: Negative;
(21) Major diamino acid of cell wall:
　　Lysine; and
　　(22) Mol% guanine (G) plus cytosine (C) of DNA : 63%.

The bacteriological properties were compared with those of known microorganisms with reference to *Bergey's Manual of Systematic Bacteriology*, Vol. 2 (1986). As a result, it was revealed that the microorganism was identified as a microorganism of the genus Arthrobacter. The microorganism is characteristic in that it produces a non-reducing saccharide-forming enzyme to form non-reducing saccharides having a trehalose structure when allowed to act on reducing partial starch hydrolysates, and a novel trehalose-releasing enzyme which specifically hydrolyzes the linkage between a trehalose moiety and the remaining glycosyl moiety in a non-reducing saccharide to release the trehalose moiety. No publication has reported such a microorganism having these properties.

The microorganism had been named "Arthrobacter sp. Q36" by the present inventors, and deposited on Jun. 3, 1993, in National Institute of Bioscience and Human-Technology Agency of Industrial Science and Technology, Ibaraki, Japan. The deposition of the microorganism was accepted on the same day and has been maintained by the institute under the accession number of FERM BP-4316.

In addition to the above-mentioned microorganism, other strains of the genus Arthrobacter and their mutants can be suitably used in the invention as long as they produce the present trehalose-releasing enzyme which specifically hydrolyzes the linkage between a trehalose moiety and the remaining glycosyl moiety in non-reducing partial starch hydrolysates having a trehalose structure as an end unit and having a degree of glucose polymerization of 3 or higher.

Other microorganisms can be used in the invention as long as they produce the present enzyme. For example, in addition to the above Rhizobium sp. M-11 (FERM BP-4130) and arthrobacter sp. Q36 (FERM BP-4316), other hitherto known microorganisms such as those of the species *Brevibacterium helvolum* (ATCC 11822) and *Micrococcus roseus* (ATCC 186) can be favorably used in the invention.

Any nutrient culture medium can be used in the invention as long as such microorganisms can grow therein and produce the present trehalose-releasing enzyme: For example, synthetic- and natural-nutrient culture media can be arbitrarily used. Any carbon-containing substance can be used in the invention as a carbon source as long as it is utilized by the microorganisms: Examples of such a carbon source are saccharides such as glucose, fructose, lactose, sucrose, mannitol, sorbitol, molasses and partial starch hydrolysates; and organic acids such as citric acid and succinic acid. The concentrations of these carbon sources in nutrient culture media are appropriately chosen. For example, in the case of using partial starch hydrolysates, a preferable concentration is usually 20% or lower, more particularly, 5% or lower, d.s.b., in view of the growth and proliferation of the microorganisms. The nitrogen sources usable in the invention are, for example, inorganic nitrogen compounds such as ammonium salts and nitrates; and organic nitrogen-containing substances such as urea, corn steep liquor, casein, peptone, yeast extract and beef extract. The inorganic ingredients usable in the invention are, for example, calcium salts, magnesium salts, potassium salts, sodium salts, phosphates and other salts of manganese, zinc, iron, copper, molybdenum and cobalt. If necessary, amino acids and vitamins can be favorably used.

The microorganisms usable in the invention are cultured under aerobic conditions at a temperature, usually, a temperature in the range of 4°–40° C., preferably, a temperature in the range of 20°–35° C.; and at a pH in the range of 4–10, preferably, a pH in the range of 5–9. The cultivation time suitably used in the invention is set to a time which is longer than that required for the growth initiation of the microorganisms, preferably, 10–100 hours. The concentration of dissolved oxygen (DO) in nutrient culture media is not specifically restricted, and, usually a DO in the range of 0.5–20 ppm is satisfactorily used. The concentration of DO can be kept within the range by controlling the aeration rate, stirring nutrient culture media, supplementing oxygen to aeration, and increasing the inner pressure of fermenters. The culture can be carried out batchwise or in continuous manner.

After completion of the culture of microorganisms, the present enzyme is recovered. Inasmuch as the activity of the present enzyme is found in both cells and cell-free supernatants, they can be recovered and used as a crude enzyme. The resultant culture can be used intact as a crude enzyme. Conventional liquid-solid separation methods can be employed in the invention to remove cells from the culture. For example, methods to directly centrifuge the resultant cultures and those to filtrate them with precoat filters or to separate cells by membrane filtration using plate filters or hollow fibers can be suitably used. Cell-free filtrates thus obtained can be used intact as an enzyme solution or they may be concentrated prior to their use. The concentration methods usable in the invention are, for example, salting out using ammonium sulfate, sedimentation using acetone and alcohol, and concentration using membranes such as plate filters and hollow fibers.

Cell-free filtrates and their concentrates can be subjected to conventional immobilization methods. Examples of conventional methods are conjugation methods using ion-exchangers, and covalent linkages and absorptions using resins and membranes, as well as inclusion methods using high-molecular weight substances. Cells separated from the resultant culture can be used as a crude enzyme without any further treatment or may be immobilized prior to their use. For example, the cells are immobilized by mixing them with sodium alginate, and dropping the resultant mixture in calcium chloride solution to gelatinize the drops into granules. The resultant granules can be fixed by using polyethylene imine or glutaraldehyde. Enzyme preparations extracted from cells can be used in the invention as a crude enzyme solution. Clear crude enzyme solutions containing the present enzyme can be obtained by extracting the present enzyme from cells, which were pretreated with ultrasonic, mechanical disruption using glass beads and alumina, french-press disruption, etc., and subjecting the resultant extracts to centrifugation or membrane filtration.

The crude enzyme solutions thus obtained can be used intact or purified by conventional methods prior to their use. For example, a purified enzyme preparation, which exhibits a single band on electrophoresis, can be prepared by dialyzing a crude enzyme preparation, which were prepared by salting out the crude enzyme cultures with ammonium sulfate and concentrating the resultant, and successively purifying the dialyzed solution on anion-exchange column chromatography using "DEAE-Toyopearl®", an anion exchanger; hydrophobic column chromatography using "Butyl-Toyopearl®", a hydrophobic resin; and gel filtration chromatography using "Toyopearl® HW-55", a resin for gel filtration, all of which are products of Tosoh Corporation, Tokyo, Japan.

The present trehalose-releasing enzyme thus obtained has the following physicochemical properties:

(1) Action

Specifically hydrolyzing the linkage between a trehalose moiety and the remaining glycosyl moiety in a non-reducing saccharide having a trehalose structure as an end unit and having a degree of glucose polymerization of 3 or higher;

(2) Molecular weight

About 57,000–68,000 daltons on sodium dodecylsulfate-polyacrylamide gel electrophoresis (SDS-PAGE);

(3) Isoelectric point (pI)

About 3.3–4.6 on isoelectrophoresis using ampholyte;

(4) Optimum temperature

About 35°–45° C. when incubated at pH 7.0 for 30 min;

(5) Optimum pH

About 6.0–7.5 when incubated at 40° C. for 30 min;

(6) Thermal stability

Stable up to a temperature of about 30°–45° C. when incubated at pH 7.0 for 60 min; and (7) pH Stability Stable at a pH of about 5.0–10.0 when incubated at 25° C. for 16 hours.

The activity of the present trehalose-releasing enzyme is assayed as follows: One ml of an enzyme solution is added to 4 ml of 1.25 w/v % maltotriosyltrehalose alias α-maltotetraosyl α-glucoside in 50 mM phosphate buffer (pH 7.0), and the mixture solution is incubated at 40° C. for 30 min. To the resultant reaction mixture is added a copper solution for the Somogyi reaction to suspend the enzymatic reaction, followed by the determination of the reducing power on the Somogyi-Nelson's method. As a control, an enzyme solution, which were preheated at 100° C. for 10 min to inactivate the enzyme, is assayed similarly as above. One unit activity of the present enzyme is defined as the amount of enzyme which increases the reducing power of that of one μmole of glucose per minute when assayed with the above-mentioned assay.

Any substance can be used as a substrate for the present enzyme as long as it is a non-reducing saccharide having a trehalose structure as an end unit and having a degree of glucose polymerization of 3 or higher: Examples of such a substrate are glycosyltrehaloses such as glucosyltrehalose, maltosyltrehalose, maltotriosyltrehalose, maltotetraosyltrehalose and maltopentaosyltrehalose which are prepared by allowing a non-reducing saccharide-forming enzyme to act on maltotriose, maltotetraose, maltopentaose, maltohexaose and maltoheptaose. In addition to these substrates, relatively-low reducing partial starch hydrolysates, having a trehalose structure as an end unit and having a degree of glucose polymerization of 3 or higher, which can be prepared by partially hydrolyzing amylaceous substances such as starch, amylopectin and amylose with amylases or acids can be suitably used in the invention.

Examples of such amylases which partially hydrolyzing starch are α-amylase, maltopentaose-forming amylase and maltohexaose-forming amylase as disclosed in *Handbook of Amylases and Related Enzymes*, published by Pergamon Press, Tokyo, Japan (1988). These amylases can be used in combination with debranching enzymes such as pullulanase and isoamylase.

The concentration of the reducing partial starch hydrolysates used as a substrate in the invention is not specifically restricted. The enzymatic reaction according to the present invention proceeds even in a solution containing 0.1% or 50% of a substrate to form trehalose. Suspensions containing insoluble substrates can be used in the invention. The reaction temperature usable in the present enzymatic reaction can be set to a temperature at which the present enzyme is not inactivated, i.e. a temperature up to about 55° C., preferably, a temperature in the range of 40°–55° C. The reaction pH usable in the present enzymatic reaction is set to a pH in the range of 5–10, preferably, a pH in the range of about 6–8. The reaction time usable in the present enzymatic reaction is adequately chosen dependently on the conditions of the enzymatic reaction, and, usually it is in the range of about 0.1–100 hours when the present enzyme is used in an amount of about 0.1–100 units/g substrate, d.s.b.

As regards the yield of trehalose from material substrates, specifically, in the case of preparing trehalose from non-reducing partial starch hydrolysates with a relatively-low DE value, i.e. those with a relatively-high degree of glucose polymerization, the present preparation of trehalose has the advantage of that it increases the yield of trehalose more than that attained by a preparation as disclosed in Japanese Patent Application No.362,131/92 wherein a non-reducing saccharide-forming enzyme and glucoamylase are used in combination. The present preparation, wherein a non-reducing saccharide-forming enzyme and the present trehalose-releasing enzyme are used in combination, forms trehalose in a high yield of about 60% or higher, while the preparation of the Japanese Patent Application forms trehalose only in a yield of about 30%.

The enzymatic mechanism of the present invention is as follows: A reducing partial starch hydrolysate with a relatively-high degree of glucose polymerization is first converted by a non-reducing saccharide-forming enzyme into one mole of a non-reducing saccharide having a trehalose structure as an end unit, then the resultant non-reducing saccharide is hydrolyzed by the present trehalose-releasing enzyme into one mole of trehalose and one mole of a reducing partial starch hydrolysate with a degree of glucose polymerization of lower than that of the material reducing partial starch hydrolysate by 2. In the case of that the newly formed reducing partial starch hydrolysate has a degree of glucose polymerization of 3 or higher, it can be further converted into a non-reducing saccharide having a trehalose structure as an end unit, and then converted into one mole of trehalose and a partial starch hydrolysate by the trehalose-releasing enzyme. Accordingly, repeated enzymatic reactions of the aforesaid non-reducing saccharide-forming enzyme and trehalose-releasing enzyme can form from one mole of a non-reducing partial starch hydrolysate one or more trehalose molecules and a non-reducing partial starch hydrolysate with a degree of glucose polymerization of lower than that of the material partial starch hydrolysate by a number of 2-fold higher than that of the formed trehalose molecules.

In the present preparation, a non-reducing saccharide-forming enzyme and the present trehalose-releasing enzyme can be simultaneously allowed to act on non-reducing partial starch hydrolysates having a degree of glucose polymerization of 3 or higher, or these two enzymes can be successively allowed to act on non-reducing partial starch hydrolysates in this order. In order to more increase the trehalose yield, the resultant reaction mixture can be further subjected to the action of glucoamylase.

The reaction mixtures thus obtained are in usual manner subjected to filtration and centrifugation to remove insoluble substances, and the resultant solutions are decolored with an activated charcoal, desalted with ion-exchangers in H and OH-form, and concentrated into syrupy products. The syrupy products can be arbitrarily dried into powdery products.

If necessary, the powdery products are readily processed into high-purity trehalose products by purifying them with one or more methods, for example, fractionations on ion-exchange column chromatography, column chromatography using an activated charcoal or a silica gel; separations using organic solvents such as alcohol and acetone; and alkaline treatments to decompose and remove the remaining reducing saccharides.

If necessary, the saccharide products containing the trehalose according to the invention can be hydrolyzed by α-amylase, β-amylase, glucoamylase, α-glucosidase and/or trehalase, or subjected to a saccharide-transfer reaction by using cyclomaltodextrin glucanotransferase and/or glucosyltransferase to control their sweetness and reducing power as well as to reduce their viscosity. Furthermore, the saccharide products can be arbitrarily hydrogenated to convert them into sugar alcohols to eliminate their reducing power. From the resultant products glucose can be removed by using aforesaid purification methods such as ion-exchange column chromatography to prepare high trehalose content fractions. The fractions thus obtained can be readily purified and concentrated into syrupy products, and, if necessary the syrupy products can be further concentrated into supersaturated solutions and crystallized to obtain hydrous crystalline trehalose or anhydrous crystalline trehalose.

The ion-exchange column chromatographic techniques usable in the invention include, for example, those which employ a strong-acid cation-exchange resin as disclosed in Japanese Patent Laid-Open Nos. 23,799/83 and 72,598/83. By using the techniques, concomitant saccharides contained in crude trehalose products can be readily removed to obtain high trehalose content products. In this case, any one of fixed-bed, moving bed and semi-moving methods can be arbitrarily employed.

In order to prepare hydrous crystalline trehalose, an about 65–90% trehalose solution is placed in a crystallizer, and gradually cooled while stirring in the presence of 0.1–20% seed crystal at a temperature of 95° C. or lower, preferably, a temperature in the range of 10°–90° C., to obtain a massecuite containing hydrous crystalline trehalose. Conventional methods such as separation, block pulverization, fluidized-bed granulation and spray drying can be employed in the invention to prepare from the massecuite hydrous crystalline trehalose or crystalline saccharides containing it.

In the case of separation, massecuites are usually subjected to a basket-type centrifuge to separate hydrous crystalline trehalose from the mother liquor, and, if necessary the hydrous crystalline trehalose is washed by spraying it with a small amount of cold water to facilitate the preparation of hydrous crystalline trehalose with an increased purity. In the case of spray drying, crystalline saccharides with no or substantially free of hygroscopicity are readily prepared by spraying massecuites, having a concentration of 60–85%, d.s.b., and a crystallinity of about 20–60%, d.s.b., from a nozzle by a high-pressure pump; drying the resultants with an about 60°–100° C. hot air which does not melt the resultant crystalline powders; and aging the resultant powders for about 1–20 hours while blowing thereto an about 30°–60° C. hot air. In the case of block pulverization, crystalline saccharides with no or substantially free of hygroscopicity are readily prepared by allowing massecuites, having a moisture content of about 10–25% and a crystallinity of about 10–60%, d.s.b., to stand for several hours to 3 days or so in order to crystallize and solidify the whole contents into blocks, pulverizing or cutting the resultant blocks, and drying the resultants. Although anhydrous crystalline trehalose can be prepared by drying hydrous crystalline trehalose to convert it into anhydrous form, it is generally prepared by providing a high trehalose content solution with a moisture content less than 10%, placing the solution in a crystallizer, keeping the solution in the presence of a seed crystal at a temperature in the range of 50°–160° C., preferably, a temperature in the range of 80°–140° C. under stirring conditions to obtain a massecuite containing anhydrous crystalline trehalose, crystallizing it, and pulverizing the resultant anhydrous crystalline trehalose under dryness and relatively-high temperature conditions by conventional methods such as block pulverization, fluidized-bed granulation and spray drying.

The present trehalose thus obtained is stable and substantially free of reducing power, and can be mixed and processed with other materials, specifically, amino acids and amino acid-containing substances such as oligopeptides and proteins without a fear of causing unsatisfactory browning and smell as well as deterioration of the materials. Trehalose per se has a satisfactorily-high quality and sweetness. Since trehalose is readily hydrolyzed by trehalase into glucose units, it is assimilated, absorbed and utilized by living bodies as a caloric source when orally administered. Furthermore, trehalose is not substantially fermented by dental carries-inducing microorganisms, and this renders it useful as a sweetener substantially free of inducing dental caries.

The present trehalose can be prepared into agents, for example, nutritional agents for transfusion and intubation feeding, which are arbitrarily administrable to living bodies and readily metabolized and utilized by the living bodies without a fear of causing toxicity and side effects. Thus, these products can be advantageously used as an energy-supplementing agent for living bodies.

Trehalose is a stable sweetener, and, especially crystalline trehalose is arbitrarily used as a sugar coating agent for tablets when used in combination with a binder such as pullulan, hydroxyethyl starch or polyvinylpyrrolidone. In addition, trehalose has properties such as osmotic pressure-controlling ability, filler-imparting ability, gloss-imparting ability, moisture-retaining ability, viscosity-imparting ability, substantial no fermentability, ability to prevent retrogradation of gelatinized starch, and ability to prevent crystallization of other saccharides.

Thus, the present trehalose and saccharide composition containing the same can be arbitrarily used as a sweetener, taste-improving agent, quality-improving agent, stabilizer and filler in a variety of compositions such as food products, cigarettes, tobaccos, feeds, cosmetics and pharmaceuticals.

The present trehalose and saccharide compositions containing the same can be used intact as a seasoning for sweetening. If necessary, they can be used together with adequate amounts of one or more other sweeteners, for example, powdered syrup, glucose, fructose, maltose, sucrose, isomerized sugar, honey, maple sugar, erythritol, sorbitol, maltitol, lactitol, dihydrocharcone, stevioside, α-glycosyl stevioside, rebaudioside, glycyrrhizin, L-aspartyl L-phenylalanine methyl ester, saccharin, glycine and alanine; and/or a filler such as dextrin, starch and lactose.

The present trehalose and saccharide compositions containing the same in the form of a powder or a crystal can be used intact, or, if necessary they can be mixed with an excipient, filler, diluent and binder and formed into granules, spheres, shot-rods, plates, cubes and tablets, prior to their use.

The present trehalose and saccharide compositions containing the same well harmonize with other materials having sour-, acid-, salty-, bitter-, astringent- and delicious-tastes, and have a relatively-high acid tolerance and heat resistance. Thus, they can be favorably used in food products in general as a sweetener, taste-improving agent and quality-improving agent.

The present trehalose and saccharide compositions containing the same can be used in seasonings such as an amino acid, peptide, soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), nucleic acid condiments, mixed seasoning, "mirin" (a sweet sake), "shin-mirin" (a synthetic mirin), table sugar and coffee sugar.

The present trehalose and saccharide compositions containing the same can be also used freely for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products; canned and bottled products such as those of meat, fish meat, fruit and vegetable; alcoholic beverages such as synthetic sake, wine and liquors; soft drinks such as coffee, tea, cocoa, juice, carbonated beverage, sour milk beverage and beverage containing a lactic acid bacterium; instant food products such as instant pudding mix, instant hot cake mix and "sokuseki-shiruco" (an instant mix of adzuki-bean soup with rice cake) and instant soup mix; and beverages such as baby foods, foods for therapy, and beverages supplemented with nutrition; as well as for improving the tastes and qualities of the aforementioned food-products.

The present trehalose and saccharide compositions containing the same can be also used in feeds and pet foods for animals such as domestic animals, poultry, honey bees, silk worms and fishes in order to improve their taste preferences. The trehalose and saccharide compositions can be arbitrarily used as a sweetener, taste-improving agent, quality-improving agent and stabilizer in other products in paste and liquid form such as a tobacco, cigarette, dentifrice, lipstick, rouge, lip cream, internal medicine, tablet, troche, cod liver oil in the form of a drop, cachou, oral refrigerant, gargle, cosmetic and pharmaceutical.

The present trehalose and saccharide compositions containing the same can be used as a quality-improving agent and stabilizer for biologically active substances susceptible to loss of their effective ingredients and activities, as well as in health foods and pharmaceutical compositions containing biologically active substances. Examples of such a biologically active substance are lymphokines such as $\alpha$-, $\beta$- and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor and interleukin 2 (IL-2); hormones such as insulin, growth hormone, prolactin, erythropoietin and follicle-stimulating hormone; biological preparations such as BCG vaccine, Japanese encephalitis vaccine, measles vaccine, live polio vaccine, smallpox vaccine, tetanus toxoid, Trimeresurus antitoxin and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, $\beta$-amylase, isoamylase, glucanase and lactase; extracts such as ginseng extract, snapping turtle extract, chlorella extract, aloe extract and propolis extract; viable microorganisms such as viruses, lactic acid bacteria and yeasts; and other biologically active substances such as royal jelly. By using the present trehalose and saccharide compositions containing the same, the aforementioned biologically active substances are readily prepared into health foods and pharmaceutical compositions with a satisfactorily-high stability and quality without a fear of losing or inactivating their effective ingredients and activities.

As described above, the methods to incorporate the present trehalose and saccharide compositions containing the same into the aforementioned substances and compositions include conventional methods, for example, mixing, kneading, dissolving, melting, soaking, permeating, sprinkling, applying, coating, spraying, injecting, crystallizing and solidifying. The trehalose and saccharide compositions containing the same are usually incorporated into the aforementioned substances and compositions in an amount of 0.1% or higher, preferably, one % or higher, d.s.b.

The following experiments explain the production and purification of the present trehalose-releasing enzyme derived from microorganisms of the species Rhizobium sp. M-11 and Arthrobacter sp. Q36, as well as hitherto known microorganisms:

EXPERIMENT 1

Production of trehalose-releasing enzyme by Rhizobium sp. M-11

A liquid nutrient culture medium, consisting of 2.0 w/v % "PINE-DEX #4", a starch product of Matsutani Chemical Ind., Co., Ltd., Kyoto, Japan, 0.5 w/v % peptone, 0.1 w/v % yeast extract, 0.1 w/v % disodium hydrogenphosphate, 0.1 w/v % potassium hydrogenphosphate and water, was adjusted to pH 7.0. About 100 ml aliquots of the liquid nutrient culture medium were placed in 500-ml Erlenmeyer flasks, autoclaved at 120° C. for 20 min to effect sterilization, cooled, inoculated with a seed culture of Rhizobium sp. M-11 (FERM BP-4130), and incubated at 27° C. for 24 hours under stirring conditions of 130 rpm. The resultant cultures were pooled and used as a seed culture.

About 20 L of a fresh preparation of the same liquid nutrient culture medium as used in the above culture was placed in a 30-L fermenter, sterilized, cooled to 27° C., inoculated with one w/v % of the seed culture, and incubated for about 72 hours under stirring and aerobic conditions at 27° C. and a pH of 6.0–8.0.

The activities of a non-reducing saccharide-forming enzyme and the present trehalose-releasing enzyme accumulated in the culture were respectively about 1.5 units/ml and about 2 units/ml. A portion of the culture was separated by centrifugation into cells and a supernatant, and the cells were suspended in 50 mM phosphate buffer (pH 7.0) to give the same volume of the portion, followed by assaying the enzyme activity of the cell suspension and the supernatant. The activities of the non-reducing saccharide-forming enzyme and the present trehalose-releasing enzyme in the cell suspension were respectively about 0.6 units/ml and about 0.8 units/ml, and the culture supernatant contained about 0.9 units/ml of the non-reducing saccharide-forming enzyme and about 1.2 units/ml of the present trehalose-releasing enzyme.

The assay of the non-reducing saccharide-forming enzyme is as follows: One ml of an enzyme solution is added to 4 ml of 1.25 w/v % maltopentaose in 50 mM phosphate buffer (pH 7.0), and the mixture solution is incubated at 40° C. for 10 min and heated at 100° C. for 10 min to suspend the enzymatic reaction. The resultant reaction mixture is precisely diluted with a buffer by 10 times, and the reducing power was determined on the Somogyi-Nelson's method. As a control, an enzyme solution, preheated at 100° C. for 10 min to inactivate the enzyme, is assayed similarly as above. One unit activity of the non-reducing saccharide-forming enzyme is defined as the amount of enzyme which eliminates the reducing power of that of one μmole of maltopentaose per minute when assayed with the above-mentioned assay.

EXPERIMENT 2

Purification of enzyme

An about 18 L of a culture obtained by the method in Experiment 1 was treated to disrupt cells with "MINI-RABO", a supper high-pressure cell disrupting apparatus commercialized by Dainippon Pharmaceutical Co., Ltd., Tokyo, Japan. The resultant suspension was centrifuged at 10,000 rpm for 30 min to obtain an about 16 L supernatant. Ammonium sulfate was added to the supernatant and dissolved therein to give a saturation degree of 0.2, and the resultant solution was allowed to stand at 4° C. for one hour, and centrifuged at 10,000 rpm for 30 min to obtain a supernatant.

Ammonium sulfate was added to the resultant supernatant and dissolved therein to give a saturation degree of 0.6, and the resultant solution was centrifuged at 10,000 rpm for 30 min, followed by recovering a precipitate and dissolving it in 10 mM phosphate buffer (pH 7.0). The solution thus obtained was dialyzed against a fresh preparation of the same phosphate buffer for 24 hours, and centrifuged at 10,000 rpm for 30 min to remove insoluble substances. Three hundred and sixty ml of the resultant dialyzed solution was divided into 2 portions which were then separately subjected to column chromatography using a column packed with 300 ml of "DEAE-Toyopearl®", an ion-exchanger commercialized by Tosoh Corporation, Tokyo, Japan.

The objective non-reducing saccharide-forming enzyme and trehalose-releasing enzyme were adsorbed on the ion-exchanger, and eluted separately from the column with a fresh preparation of the same phosphate buffer supplemented with salt at different salt concentrations. The elution pattern of the column or the column chromatogram was as shown in FIG. 1. The non-reducing saccharide-forming enzyme was eluted from the column at a salt concentration of about 0.2M, while the trehalose-releasing enzyme was eluted from the column at a salt concentration of about 0.3M. The fractions containing either of the objective enzymes were separately pooled and purified.

The pooled fractions containing the non-reducing saccharide-forming enzyme were dialyzed against a fresh preparation of the same phosphate buffer supplemented with 2M ammonium sulfate. The dialyzed solution was centrifuged at 10,000 rpm for 30 min to remove insoluble substances, and the resultant supernatant was subjected to hydrophobic column chromatography using a column packed with 300 ml of "Butyl-Toyopearl® 650", a hydrophobic gel commercialized by Tosoh Corporation, Tokyo, Japan. The enzyme adsorbed on the gel was eluted from the column with a liner gradient buffer ranging from 2M to 0M, followed by recovering fractions with the enzyme activity. The resultant fractions were subjected to gel filtration chromatography using a column packed with 300 ml of "Toyopearl® HW-55", a resin for gel chromatography commercialized by Tosoh Corporation, Tokyo, Japan, followed by recover fractions with the enzyme activity.

By using the pooled fractions with a trehalose-releasing enzyme activity eluted from the column of "DEAE-Toyopearl®", the fractions were treated similarly as in the purification steps used in the preparation of the non-reducing saccharide-form enzyme in such a manner that they were dialyzed against a buffer containing 2M ammonium sulfate, and successively subjected to hydrophobic column chromatography and Gel filtration chromatography.

The total enzyme activity, specific activity and yield of the non-reducing saccharide-form enzyme in each purification step are as shown in Table 1, while those of the trehalose-releasing enzyme are as shown in Table 2.

TABLE 1

| Purification step | Total enzyme* activity (units) | Specific activity (units/mg protein) | Yield (%) |
| --- | --- | --- | --- |
| Material culture | 28,500 | — | 100 |
| Supernatant after cell disruption | 22,900 | 0.12 | 80 |
| Dialyzed solution after salting out | 21,100 | 0.43 | 74 |
| Eluate from ion-exchange column | 15,200 | 6.2 | 53 |
| Eluate from hydrophobic column | 7,950 | 101 | 28 |
| Eluate after gel filtration column | 5,980 | 197 | 21 |

Note: The symbol "*" means a non-reducing saccharide-forming enzyme.

TABLE 2

| Purification step | Total enzyme** activity (units) | Specific activity (units/mg protein) | Yield (%) |
| --- | --- | --- | --- |
| Material culture | 37,400 | — | 100 |
| Supernatant after cell disruption | 31,500 | 0.17 | 84 |
| Dialyzed solution after salting out | 29,200 | 0.60 | 78 |
| Eluate from ion-exchange column | 25,400 | 5.3 | 68 |

TABLE 2-continued

| Purification step | Total enzyme** activity (units) | Specific activity (units/mg protein) | Yield (%) |
| --- | --- | --- | --- |
| Eluate from hydrophobic column | 18,700 | 98.5 | 50 |
| Eluate from gel filtration column | 11,600 | 240 | 31 |

Note: The symbol "**" means the present trehalose-releasing enzyme.

The purified enzyme preparations, obtained as an eluate from gel filtration column in Tables 1 and 2, were examined their purity on electrophoresis using 7.5% polyacrylamide gel. As a result, each enzyme preparation was observed as a single protein band, and this meant that it was an electrophoretically-homogeneous preparation with a relatively-high purity.

EXPERIMENT 3

Property of trehalose-releasing enzyme

A portion of a purified trehalose-releasing enzyme preparation, obtained by the method in Experiment 2, was subjected to electrophoresis using a gel containing 10% sodium dodecylsulfate polyacrylamide, and determined its molecular weight to be about 57,000–68,000 daltons by comparing it with marker proteins commercialized by Japan Bio-Rad Laboratories, Tokyo, Japan.

Another portion of the purified enzyme preparation was subjected to isoelectrophoresis using polyacrylamide gel containing 2 v/v % "AMPHOLINE", an ampholyte commercialized by Pharmacia LKB Biotechnology AB, Uppsala, Sweden. The resultant gel was sliced into pieces, followed by measuring their pHs and resulting in a pI of the enzyme being about 3.3–4.3.

Figure 3:
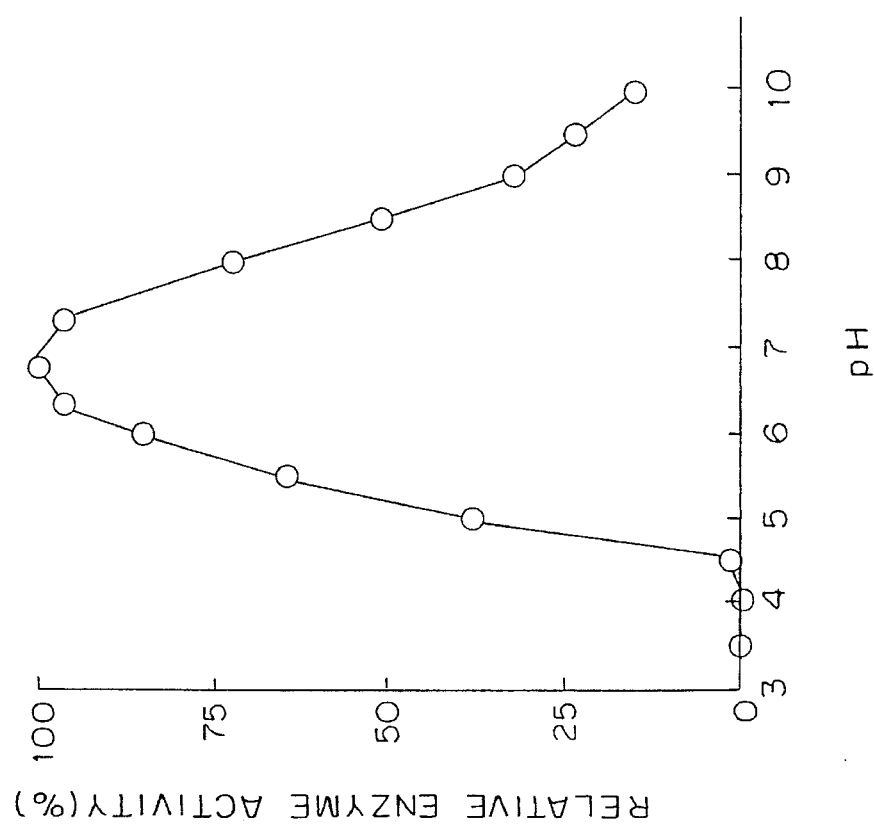
FIG. 3 shows the influence of pH on the activity of the present trehalose-releasing enzyme derived from a microorganism of the species Rhizobium sp. M-11.
Figure 2:
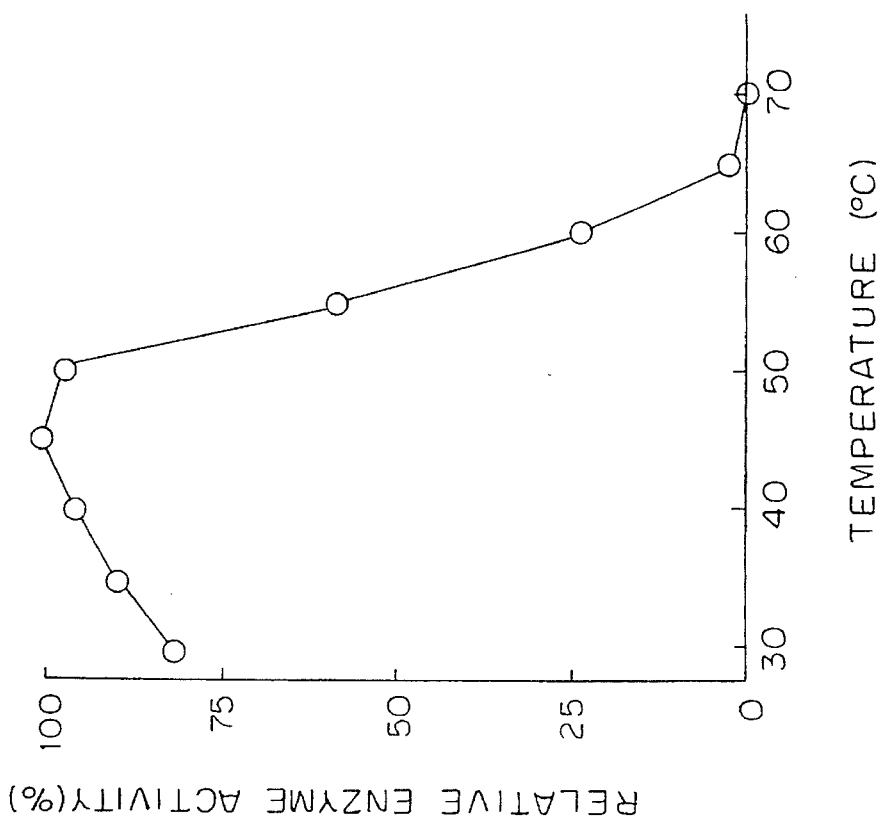
FIG. 2 shows the influence of temperature on the activity of the present trehalose-releasing enzyme derived from a microorganism of the species Rhizobium sp. M-11.
Figure 5:
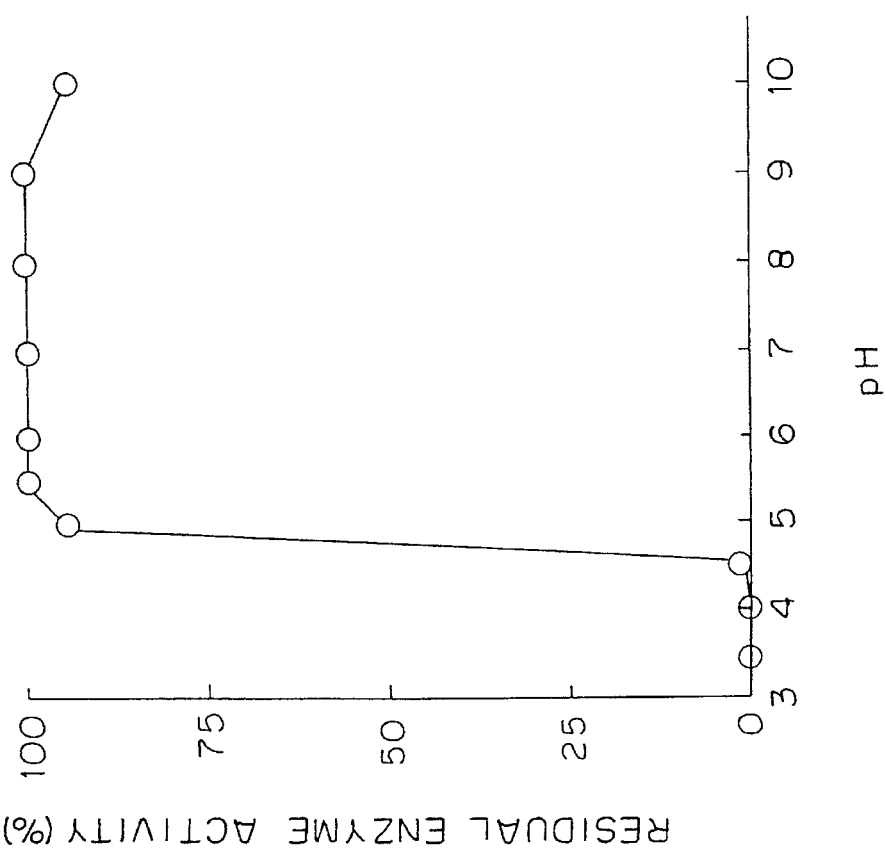
FIG. 5 shows the influence of pH on the stability of the present trehalose-releasing enzyme derived from a microorganism of the species Rhizobium sp. M-11.
Figure 4:
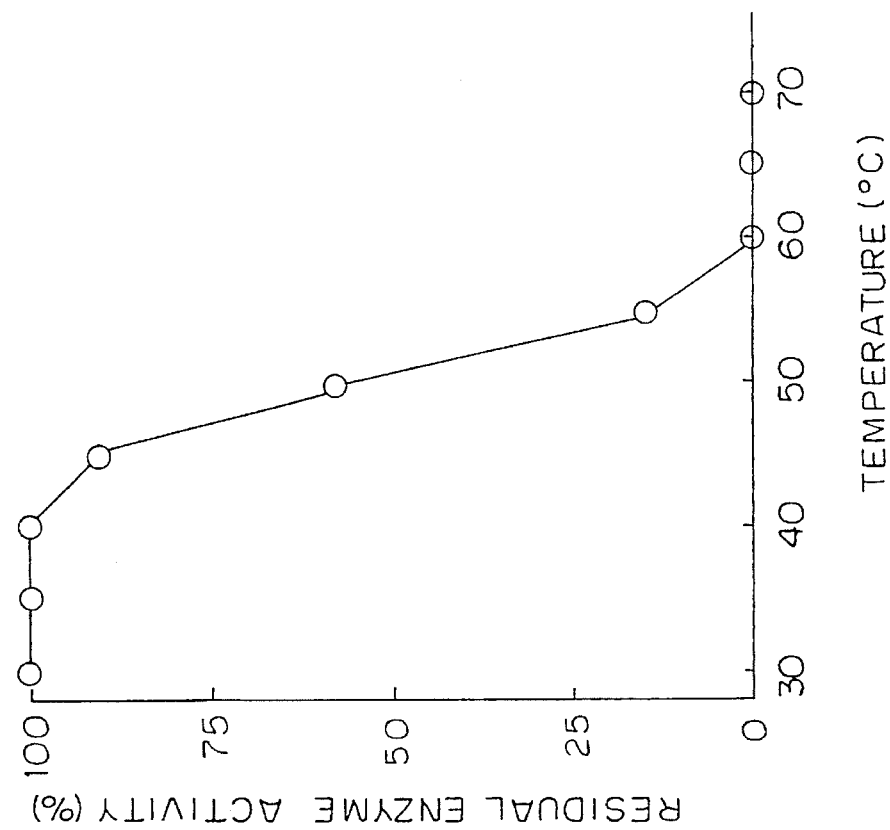
FIG. 4 shows the influence of temperature on the stability of the present trehalose-releasing enzyme derived from a microorganism of the species Rhizobium sp. M-11.
Figure 7:
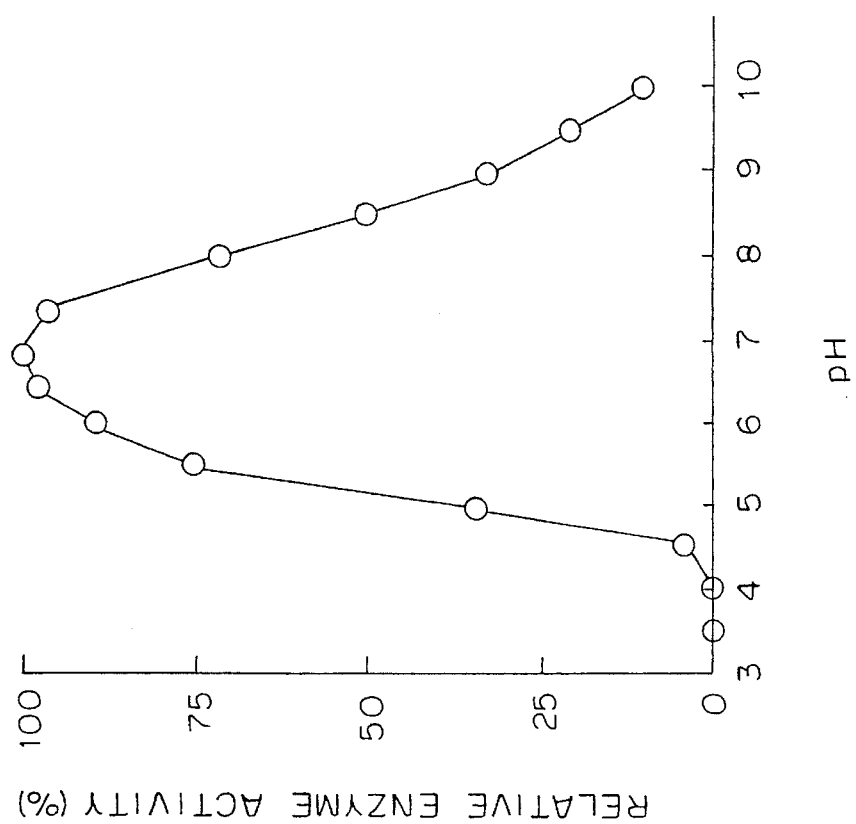
FIG. 7 shows the influence of pH on the activity of the present trehalose-releasing enzyme derived from a microorganism of the species Arthrobacter sp. Q36.
Figure 6:
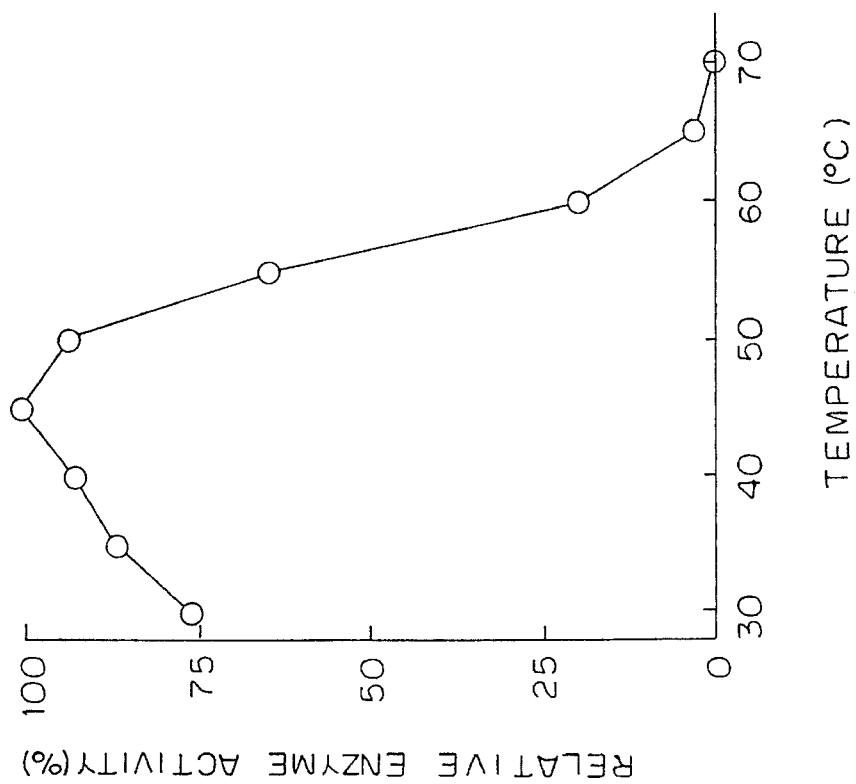
FIG. 6 shows the influence of temperature on the activity of the present trehalose-releasing enzyme derived from a microorganism of the species Arthrobacter sp. Q36.
Figure 8:
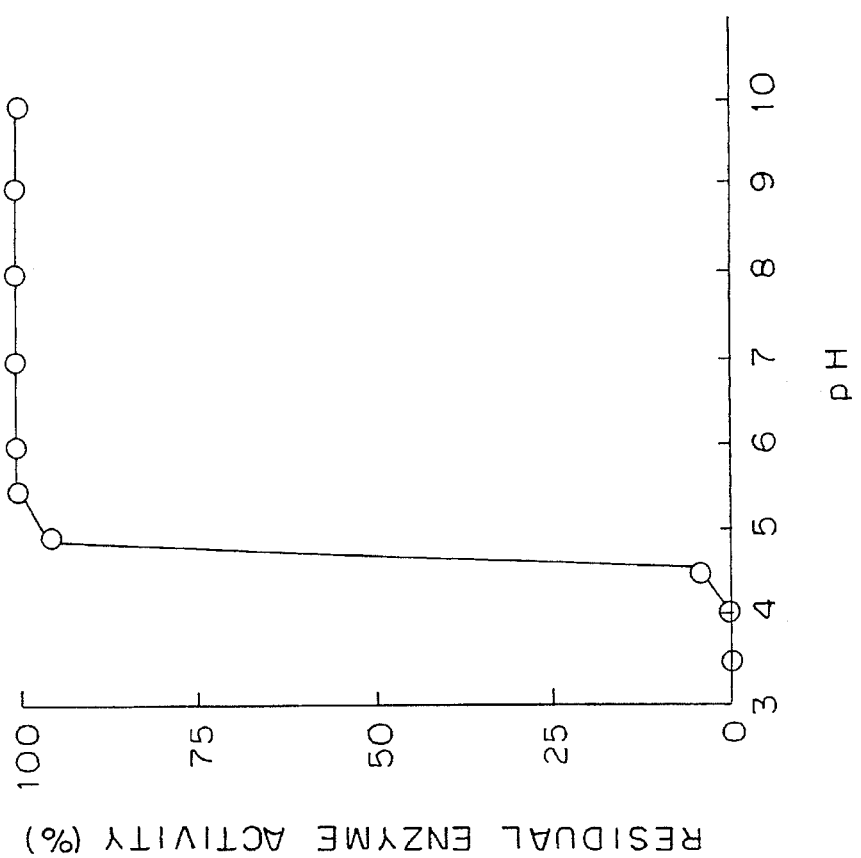
FIG. 8 shows the influence of temperature on the stability of the present trehalose-releasing enzyme derived from a microorganism of the species Arthrobacter sp. Q36.
Figure 9:
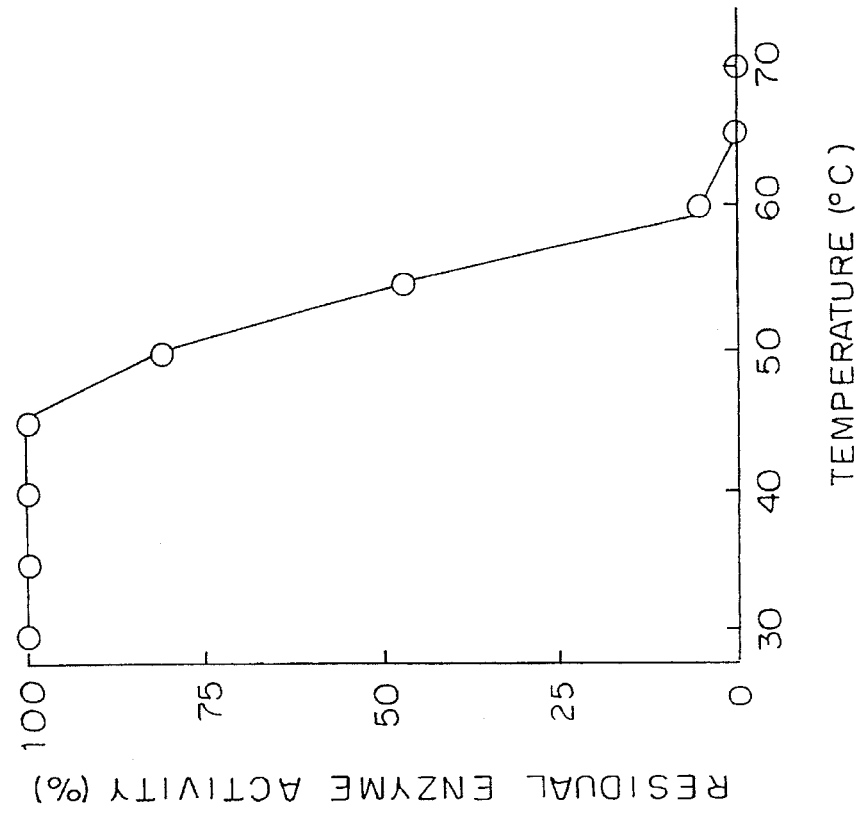
FIG. 9 shows the influence of pH on the stability of the present trehalose-releasing enzyme derived from a microorganism of the species Arthrobacter sp. Q36.

Effects of temperature and pH on the activity of the present enzyme were studied in accordance with the assay for the enzyme activity. These results were respectively shown in FIG. 2 (effect of temperature) and FIG. 3 (effect of pH). The optimum temperature of the enzyme was about 45° C. when incubated at pH 7.0 for 30 min, and the optimum pH was about 6.0–7.5 when incubated at 40° C. for 30 min. The thermal stability of the enzyme was determined by incubating it in 50 mM phosphate buffers (pH 7.0) for 60 min at different temperatures, cooling the buffers in test tubes with cold water, and determining the remaining enzyme activity $i_o$ each buffer. The pH stability of the enzyme was determined by incubating it in 50 mM phosphate buffers having different pHs at 25° C. for 16 hours, adjusting the buffers to pH 7, and assaying the remaining enzyme activity in each buffer. The results of the thermal- and pH-stabilities of the enzyme were respectively shown in FIGS. 4 and 5. The enzyme was stable up to a temperature of about 40° C. and at a pH of about 5–10.

EXPERIMENT 4

Preparation of trehalose from non-reducing saccharides having a trehalose structure as an end unit and a degree of glucose polymerization of 3 or higher Non-reducing saccharides, having a trehalose structure as an end unit and a degree of glucose polymerization of 3 or higher used as a substrate, were prepared according to the method as described in Japanese Patent Application No. 362,131/92. To an aqueous solution containing 20% maltotriose, maltotetraose, maltopentaose, maltohexaose or maltoheptaose as a substrate was added 2 units/g substrate, d.s.b., of a purified enzyme preparation obtained by the method in Experiment 2, and the resultant mixture was subjected to an enzymatic reaction at 40° C. and pH 7.0 for 48 hours. The reaction mixture was heated to inactivate the remaining enzyme, filtered, decolored, desalted and concentrated to obtain a concentrated saccharide solution which was then column chromatographed by using "XT-1016 ($Na^+$-form, polymerization degree of 4%)", an ion-exchanger commercialized by Tokyo Organic Chemical Industries, Ltd., Tokyo, Japan. In the column chromatography, the ion-exchanger was packed in 3-jacketed stainless-steel columns, having an inner diameter of 2.0 cm and a length of one m, which were then cascaded in series, heated to give the inner column temperature of 55° C., applied with 5 v/v % of the concentrated saccharide solution against the resin while keeping at 55° C., and fed with 55° C. hot water at SV (space velocity) of 0.13 to obtain high-purity non-reducing saccharides having a trehalose structure as an end unit and having a degree of polymerization of 3 or higher. Among the resultant preparations, a glucosyltrehalose preparation contained glucosyltrehalose with a purity of 97.6%, d.s.b., and the purities of maltosyltrehalose, maltotriosyltrehalose, maltotetraosyl-trehalose and maltopentaosyltrehalose in their high-purity preparations were respectively 98.6%, 99.6%, 98.3% and 98.1%, d.s.b.

An aqueous solution containing 20%, d.s.b., of each one of the above 5 non-reducing saccharide preparations, namely glycosyltrehalose preparations, was prepared, followed by mixing it with 2 units/g substrate, d.s.b., of the purified trehalose-releasing enzyme obtained in Experiment 2, and subjecting the resultant solution to an enzymatic reaction at 40° C. and pH 7.0 for 48 hours. The resultant each reaction mixture was desalted, and analyzed for its composition on high-performance liquid chromatography (HPLC) using "WAKOBEADS WB-T-330 column", a column of Wako Pure Chemical Industries Ltd., Tokyo, Japan. As a control, a fresh preparation of the same trehalose-releasing enzyme was allowed to act on maltooligosaccharides such as maltotriose, maltotetraose, maltopentaose, maltohexaose and maltoheptaose, and the resultant each reaction mixture was analyzed for its composition on HPLC. The results were as shown in Table 3.

TABLE 3

| Substrate | Product | Elution time on HPLC (min) | Percentage (%) |
| --- | --- | --- | --- |
| Glucosyltrehalose | Trehalose | 27.4 | 17.5 |
|  | Glucose | 33.8 | 6.5 |
|  | Glucosyltrehalose | 23.3 | 76.0 |
| Maltosyltrehalose | Trehalose | 27.4 | 44.3 |
|  | Maltose | 28.7 | 44.4 |
|  | Maltosyltrehalose | 21.6 | 11.3 |

TABLE 3-continued

| Substrate | Product | Elution time on HPLC (min) | Percentage (%) |
|---|---|---|---|
| Maltotriosyltrehalose | Trehalose | 27.4 | 39.5 |
| | Maltotriose | 25.9 | 60.0 |
| | Maltotriosyltrehalose | 19.7 | 0.5 |
| Maltotetraosyltrehalose | Trehalose | 27.4 | 34.2 |
| | Maltotetraose | 24.1 | 65.5 |
| | Maltotetraosyltrehalose | 18.7 | 0.3 |
| Maltopentaosyltrehalose | Trehalose | 27.4 | 29.1 |
| | Maltopentaose | 22.6 | 70.6 |
| | Maltopentaosyltrehalose | 17.8 | 0.3 |
| Maltotriose | Maltotriose | 25.9 | 100 |
| Maltotetraose | Maltotetraose | 24.1 | 100 |
| Maltopentaose | Maltopentaose | 22.6 | 100 |
| Maltohexaose | Maltohexaose | 21.8 | 100 |
| Maltoheptaose | Maltoheptaose | 21.0 | 100 |

The results in Table 3 evidently show that:

1. Trehalose-releasing enzyme according to the present invention specifically hydrolyzes the linkage between a trehalose moiety and a glycosyl moiety in a non-reducing saccharide having a trehalose structure as an end unit and having a degree of glucose polymerization of 3 or higher to form trehalose and a non-reducing saccharide having a degree of glucose polymerization of one or more; and 2. Maltooligosaccharides are not hydrolyzed by the present trehalose-releasing enzyme.

From these results, it is confirmed that the trehalose-releasing enzyme according to the present invention is a novel enzyme which has a mechanism of specifically hydrolyzing the linkage between a trehalose moiety and the remaining glycosyl moiety in a non-reducing saccharide having a trehalose structure as an end unit and having a degree of glucose polymerization of 3 or higher to release trehalose from the non-reducing saccharide.

In order to purify trehalose in each reaction mixture, the reaction mixture was subjected to column chromatography using a column packed with "XT-1016 ($Na^+$-form)", an alkaline-metal strong-acid cation exchange resin commercialized by Tokyo Organic Chemical Industries, Ltd., Tokyo, Japan, followed by recovering fractions containing 97% or higher of trehalose. The fractions were pooled and concentrated into an about 65% solution, and the concentrate was allowed to stand at 25° C. for 2 days to crystallize hydrous crystalline trehalose, followed by separating and drying it in vacuo to obtain a high-purity trehalose preparation with a purity of 99% or higher, d.s.b. The yields of trehalose from glucosyltrehalose, maltosyltrehalose, maltotriosyltrehalose, maltotetraosyltrehalose and maltopentaosyltrehalose used as a substrate were respectively 9.5%, 14.9%, 16.0%, 18.5%, and 17.7%, d.s.b. The high-purity trehalose preparations and a commercially available trehalose specimen as a standard were studied on their melting point, heat of fusion, specific rotation, infrared absorption spectrum, powdery x-ray diffraction pattern, and readiness of hydrolysis by a trehalase specimen derived from pig kidney, commercialized by Sigma Chemical Co., St. Louise, USA. As a result, every trehalose preparation showed a melting point of 97.0°±0.5° C., a heat of fusion of 57.8±1.2 kJ/mole and a specific rotation of 182°±1.1°, and these values well corresponded with those of the standard trehalose specimen, while the infrared absorption spectra and powdery x-ray diffraction patterns of the trehalose preparations also well corresponded with those of the standard trehalose specimen. Similarly as the standard trehalose specimen, the trehalose preparations were decomposed into glucose units.

As evident from these results, it was confirmed that a non-reducing saccharide, which was formed by allowing the present trehalose-releasing enzyme to act on non-reducing saccharides having a trehalose structure as an end unit and having a degree of glucose polymerization of 3 or higher, was trehalose.

EXPERIMENT 5

Preparation of trehalose from non-reducing partial starch hydrolysates

A suspension containing 5% waxy corn starch was gelatinized by heating, adjusted to pH 4.5, heated to 50° C., mixed with 4,000 units/g starch, d.s.b., of an isoamylase specimen commercialized by Hayashibara Biochemical Laboratories Inc., Okayama, Japan, and subjected to an enzymatic reaction for 20 hours. The reaction mixture was autoclaved at 120° C. for 10 min, cooled to 60° C., and subjected to gel filtration column chromatography using a column packed with 750 ml of "Toyopearl® 50S gel", commercialized by Tosoh Corporation, Tokyo, Japan, to obtain reducing partial starch hydrolysates having a degree of glucose polymerization of 35–10.

Either of the reducing partial starch hydrolysates thus obtained or maltotriose having a degree of glucose polymerization of 3 as a substrate was dissolved in 10 mM phosphate buffer (pH 7.0) into a one % solution which was then mixed with 4 units/g substrate, d.s.b., of a purified non-reducing saccharide-forming enzyme and a purified trehalose-releasing enzyme prepared by the method in Experiment 2, and subjected to an enzymatic reaction at 40° C. for 24 hours. After completion of the enzymatic reaction, a portion of the resultant each reaction mixture was desalted and analyzed on HPLC to identify its composition.

The remaining each reaction mixture was heated to 50° C., adjusted to pH 4.5, admixed with 50 units/g substrate, d.s.b., of a glucoamylase specimen commercialized by Seikagaku-Kogyo Co., Ltd., Tokyo, Japan, and subjected to an enzymatic reaction for 24 hours. Similarly as above, a portion of the resultant each reaction mixture was desalted and analyzed on HPLC to analyze its composition. The results were as shown in Table 4.

TABLE 4

| Degree of glucose polymerization of reducing partial starch hydrolysate | Reaction product | Composition (%) A* | B** |
|---|---|---|---|
| 34.1 | Trehalose | 80.8 | 83.5 |
| | Glucose | 0.2 | 16.5 |
| | Reducing oligosaccharides | 14.4 | 0.0 |
| | Glycosyltrehalose | 4.6 | 0.0 |
| 26.2 | Trehalose | 79.7 | 82.5 |
| | Glucose | 0.2 | 17.5 |
| | Reducing oligosaccharides | 15.3 | 0.0 |
| | Glycosyltrehalose | 4.8 | 0.0 |
| 18.1 | Trehalose | 77.7 | 80.7 |
| | Glucose | 0.2 | 19.3 |
| | Reducing oligosaccharides | 17.0 | 0.0 |
| | Glycosyltrehalose | 5.1 | 0.0 |
| 15.2 | Trehalose | 75.0 | 78.5 |
| | Glucose | 0.3 | 21.5 |
| | Reducing oligosaccharides | 18.6 | 0.0 |
| | Glycosyltrehalose | 6.1 | 0.0 |
| 10.0 | Trehalose | 66.1 | 70.1 |
| | Glucose | 0.3 | 29.9 |
| | Reducing oligosaccharides | 27.6 | 0.0 |
| | Glycosyltrehalose | 7.7 | 0.0 |
| 3 (Maltotriose) | Trehalose | 4.2 | 20.8 |
| | Glucose | 2.1 | 79.2 |
| | Maltotriose | 65.0 | 0.0 |
| | Glucosyltrehalose | 28.7 | 0.0 |

Note: The symbol "*" means a composition after enzymatic reaction of a non-reducing saccharide-forming enzyme and the present trehalose-releasing enzyme, and the symbol "**" means a composition after enzymatic reaction of glucoamylase. In the Table, the wording "Glycosyltrehalose" means non-reducing saccharides having a trehalose structure as an end unit and having a degree of glucose polymerization degree of 3 or higher.

As is shown in Table 4, in the case of using as a substrate maltotriose having a degree of glucose polymerization of 3, the trehalose yield after enzymatic reaction of a non-reducing saccharide-forming enzyme and the present trehalose-releasing enzyme was relatively low, i.e. 4.2%, while in the case of using as a substrate partial starch hydrolysates having a degree of glucose polymerization of 10–34.1, the trehalose yield was relatively high. i.e. 66.1–80.8%. It was found that the higher the degree of glucose polymerization of material reducing partial starch hydrolysates, the higher the purity of the resultant trehalose. It was also found that the purity of the resultant trehalose can be more increased by allowing glucoamylase to act on a reaction mixture, prepared by the hydrolysis of reducing partial starch hydrolysates by the two enzymes, to hydrolyze the concomitant non-reducing saccharides, having a trehalose structure as an end unit and having a degree of glucose polymerization of 3 or higher, into trehalose and glucose molecules.

EXPERIMENT 6

Maillard reaction

A solution, containing one % of glycine, 10% of a high-purity trehalose preparation with a purity of 99.5%, d.s.b., obtained by the method in Experiment 4, and 50 mM phosphate buffer (pH 7.0), was kept at 100° C. for 90 min, followed by cooling the resultant solution, and determining its absorbance at a wave length of 480 nm in a 1-cm cell. As a control, glucose and maltose were similarly treated as above, and the resultants were subjected to determination of their absorbances at a wave length of 480 nm. The results were as shown in Table 5.

TABLE 5

| Saccharide preparation | Coloration degree (480 nm) |
|---|---|
| Trehalose (Present invention) | 0.006 |
| Glucose (Control) | 1.671 |
| Maltose (Control) | 0.926 |

As evident from the results in Table 5, it was revealed that the trehalose preparation according to the present invention only showed a slight coloration induced by the maillard reaction, i.e. the coloration degree was merely about 0.4–0.6% of those of glucose and maltose.

The results showed that the present trehalose is substantially free from the maillard reaction. Thus, the present trehalose is a saccharide which has a less fear of causing deterioration of amino acids when mixed with them.

EXPERIMENT 7

Utilization test in vivo

In accordance with the method as reported by Atsuji et al. in "Rinsho-Eiyo", Vol. 41, No. 2, pp. 200–208 (1972), 30 g of the high-purity trehalose preparation with a purity of 99.5%, d.s.b., obtained by the method in Experiment 4 was dissolved in water into 20 w/v % aqueous solution which was then orally administered to 6 healthy male volunteers, 26-, 27-, 28-, 29-, 30- and 31-year-old. The volunteers were collected their blood at a prescribed time interval, and each collected blood was assayed for its blood sugar- and insulin-levels. As a control, glucose was used. As a result, the trehalose preparation showed the same dynamics as in glucose, i.e. the blood sugar- and insulin-levels showed their maxima at an about 0.5–1 hour after their administrations. It was revealed that the trehalose preparation is readily assimilated, absorbed, metabolized and utilized by the body as an energy source.

EXPERIMENT 8

Acute toxicity test

By using mice, the high-purity trehalose preparation with a purity of 99.5%, d.s.b., obtained by the method in Experiment 4 was orally administered to the mice for its acute toxicity test. As a result, it was revealed that the trehalose preparation is a relatively-low toxic substance and no mouse died even when administered with it in an amount of the highest possible dose. Though not so accurate, the $LD_{50}$ of the trehalose preparation was 50 g/kg or higher.

EXPERIMENT 9

Production of trehalose-releasing enzyme by Arthrobacter sp. Q36

Similarly as in Experiment 1, a seed culture of Arthrobacter sp. Q36 (FERM BP-4316) was cultured by a fermenter for about 72 hours in place of Rhizobium sp. M-11 (FERM BP-4130). The activities of a non-reducing saccharide-forming enzyme and the present trehalose-releasing enzyme in the resultant culture were respectively about 1.3 units/ml and about 1.8 units/ml. Similarly as in Experiment 1, a cell suspension and a culture supernatant, prepared from the resultant culture, were assayed. The former had an about 0.5 units/ml of non-reducing saccharide-forming activity and an about 0.5 units/ml of trehalose-releasing enzyme, while the latter had an about 0.8 units/ml of non-reducing saccharide-forming enzyme and an about 1.3 units/ml of trehalose-releasing enzyme.

EXPERIMENT 10

Purification of enzyme

By using an about 18 L of a culture obtained by the method in Experiment 9, the formed non-reducing saccharide-forming enzyme was purified similarly as in Experiment 2. The results in each purification step were tabulated in Table 6.

TABLE 6

| Purification step | Enzyme* activity | Specific activity (unit) | Yield (%) (units/mg protein) |
|---|---|---|---|
| Culture | 23,700 | — | 100 |
| Supernatant after cell disruption | 22,400 | 0.15 | 95 |
| Dialyzed solution after salting out with ammonium sulfate | 20,200 | 0.51 | 85 |
| Eluate from ion-exchange column | 15,100 | 6.5 | 64 |
| Eluate from hydrophobic column | 8,450 | 115 | 36 |
| Eluate from gel filtration column | 6,120 | 217 | 26 |

Note: The symbol "*" means a non-reducing saccharide-forming enzyme.

TABLE 7

| Purification step | Enzyme** activity | Specific activity (unit) | Yield (%) (units/mg protein) |
|---|---|---|---|
| Culture | 32,500 | — | 100 |
| Supernatant after cell disruption | 30,100 | 0.19 | 93 |
| Dialyzed solution after salting out with ammonium sulfate | 25,400 | 0.72 | 78 |
| Eluate from ion-exchange column | 22,700 | 22.3 | 70 |
| Eluate from hydrophobic column | 15,200 | 215 | 47 |
| Eluate from gel filtration column | 11,600 | 497 | 36 |

Note: The symbol "**" means the present trehalose-releasing enzyme.

Purified enzyme preparations of non-reducing saccharide-forming enzyme and trehalose-releasing enzyme, obtained as the eluates from gel filtration column in Tables 6 and 7, were studied on the purities of the enzymes by using electrophoresis similarly as in Experiment 2. As a result, they were respectively observed as a single protein band, and this meant that they were relatively-high purity enzyme preparations exhibiting an electrophoretically single band.

EXPERIMENT 11

Property of enzyme

A purified trehalose-releasing enzyme preparation obtained by the method in Experiment 10 was determined its molecular weight on SDS-PAGE to give about 57,000–67,000 daltons. The pI of the enzyme preparation was determined on isoelectrophoresis similarly as in Experiment 3 to give a pI of about 3.6–4.6. The influences of temperature and pH on the enzyme activity, as well as the thermal stability and pH stability, were studied similarly as in Experiment 3. The results of the influence of temperature, influence of pH, thermal stability and pH stability were respectively as shown in FIGS. 6, 7, 8 and 9.

As evident from these FIGS., the optimum temperature of the enzyme preparation is about 45° C.; the optimum pH, about 6.0–7.5; the thermal stability, up to about 45° C.; and the pH stability, about 5.0–10.0.

EXPERIMENT 12

Preparation of trehalose from non-reducing saccharides having a trehalose structure as an end unit and having a degree of glucose polymerization of 3 or higher By using the purified enzyme preparation obtained by the method in Experiment 10, trehalose was experimentally prepared from non-reducing saccharides having a trehalose structure and having a degree of glucose polymerization of 3 or higher according to the methods in Experiment 4. As a result, it was revealed that the enzyme preparation releases trehalose from the non-reducing saccharides similarly as that derived from Rhizobium sp. M-11.

EXPERIMENT 13

Production and property of trehalose-releasing enzyme from known microorganisms

Among hitherto known microorganisms, those of the species *Brevibacterium helvolum* (ATCC 11822) and *Micrococcus roseus* (ATCC 186), which had been confirmed by the present inventors to produce the present trehalose-releasing enzyme, were respectively cultured by a fermenter at 27° C. for 72 hours similarly as in Experiment 1. Eighteen L of each resultant culture was subjected to a cell disrupting apparatus and centrifuged to obtain a supernatant which was then successively salted out with ammonium sulfate, dialyzed, and subjected to an ion-exchange column to obtain a partially purified enzyme preparation, followed by studying its properties. The results along with those of Rhizobiumsp. M-11 and Arthrobacter sp. Q36 were tabulated in Table 8.

TABLE 8

| Microorganism | Enzyme activity of eluate from ion-exchange column (unit) | Optimum temperature (°C.) | Optimum pH | Thermal stability (°C.) | pH Stability |
|---|---|---|---|---|---|
| *Brevibacterium helvolum* (ATCC 11822) | 6,070 | About 40 | About 6.5–6.8 | Up to about 40 | About 5.5–9.5 |
| *Micrococcus roseus* (ATCC 186) | 3,010 | About 35 | About 6.8 | Up to about 30 | About 6.5–7.2 |
| Rhizobium sp. M-11 (FERM BP-4130) | 25,400 | About 45 | About 6.0–7.5 | Up to about 40 | About 5.0–10.0 |
| Arthrobacter sp. Q36 (FERM BP-4316) | 22,700 | About 45 | About 6.0–7.5 | Up to about 45 | About 5.0–10.0 |

In accordance with the method in Experiment 12, trehalose was experimentally prepared from non-reducing saccharides having a trehalose structure as an end unit and having a degree of glucose polymerization of 3 or higher. As a result, it was revealed that similarly as the trehalose releasing enzyme from Rhizobium sp. M-11, every enzyme preparation forms trehalose from the non-reducing saccharides.

EXPERIMENT 14

Partial amino acid sequence of trehalose-releasing enzyme

EXPERIMENT 14 (1)

Amino acid sequence containing N-terminal

A portion of a purified enzyme preparation derived from Rhizobium sp. M-11, obtained by the method in Experiment 2, and a portion of a purified enzyme preparation derived from Arthrobacter sp. Q36, obtained by the method in Experiment 10, were dialyzed against distilled water, and about 80 μg protein of each resultant preparation was used as a sample for the determination of their amino acid sequences containing their N-terminals. The amino acid sequences were analyzed on "PROTEIN SEQUENCER MODEL 473A", an apparatus of Applied Biosystems, Inc., Foster City, USA, to reveal their 10 amino acid residues from their N-terminals. Partial amino acid sequences containing the N-terminals of the enzyme preparations were as shown in Table 9.

TABLE 9

| Origin | Partial amino acid sequence containing N-terminal |
| --- | --- |
| Rhizobium sp. M-11 (FERM BP-4130) | alanine-lysine-proline-valine-glutamine-glycine-alanine-glycine-arginine-phenylalanine (SEQ ID NO: 1) |
| Arthrobacter sp. Q36 (FERM BP-4316) | threonine-proline-threonine-tyrosine-proline-arginine-glutamic acid-arginine-alanine-lysine (SEQ ID NO: 2) |

As evident from Table 9, it was revealed that the N-terminal of the enzyme preparation from Rhizobium sp. M-11 is alanine which is followed by an amino acid sequence of lysine-proline-valine-glutamine-glycine-alanine-glycine-argininephenylalanine (SEQ ID NO: 1). In the case of the enzyme preparation from Arthrobacter sp. Q36, the N-terminal is threonine Which is followed by an amino acid sequence of proline-threonine-tyrosine-proline-arginine-glutamic acid-arginine-alaninelysine (SEQ ID NO: 2).

EXPERIMENT 14 (2)

Internal partial amino acid sequence

A portion of a purified enzyme preparation derived from Rhizobium sp. M-11, obtained by the method in Experiment 2, and a portion of a purified enzyme preparation derived from Arthrobacter sp. Q36, obtained by the method in Experiment 10, were dialyzed against 10 mM Tris-HCl buffer (pH 9.0), and the resultants were respectively diluted with a fresh preparation of the same buffer to give a concentration of about one mg/ml. To one ml aliquot of the resultant each solution was added 10 μg "LYSYL ENDOPEPTIDASE", a product of Wako Pure Chemical Industries, Ltd., Tokyo, Japan, and allowed to react at 30° C. for 22 hours to form peptides which were then separated on reverse phase high-performance liquid chromatography (reverse phase HPLC). The apparatus and conditions used to separate the peptides of the enzyme preparation from Rhizobium sp. M-11 in the reverse phase HPLC were "CAPCELL PAK C18 column", a diameter of 4.6 mm and a length of 250 mm, a product of Shiseido Co., Ltd., Tokyo, Japan; a flow rate, 0.6 ml/min; a temperature, an ambient temperature; an elution time, 60 min; and a gradient, a liner gradient of a solution containing 0.1 v/v % trifluoro acetate and acetonitrile ranging from 16–48 v/v %. The apparatus and conditions used to separate the peptides of the enzyme preparation from Arthrobacter sp. Q36 in the reverse phase HPLC were "μ-BONDAPAK C18 column" having a diameter of 2.1 mm and a length of 150 mm, a product of Waters Chromatography Div., MILLIPORE Corp., Milford, USA; a flow rate, 0.9 ml/min; a temperature, an ambient temperature; an elution time, 60 min; and a gradient, a liner gradient of a solution containing 0.1 v/v % trifluoro acetate and acetonitrile ranging from 30–55 v/v %. The peptides eluted from the columns were detected by monitoring an absorbency at a wavelength of 210 nm. From the enzyme preparation of Rhizobium sp. M-11 three peptides named as RT41, RT46 and RT54 having respective retention times of about 41, 46 and 54 were separated from other concomitant peptides, and from the enzyme preparation of Arthrobacter sp. Q36 three peptides named as AT7, AT30 and AT48 having respective retention times of about 7, 30 and 48 were separated from other concomitant peptides, followed by drying the separated peptides in vacuo and dissolving the resultants in 200 μl solutions having different concentrations of 0.1–50 v/v % acetonitrile. Each peptide specimen thus obtained was analyzed on a protein sequencer for its amino acid sequence up to 10 amino acid residues. The analyzed internal partial amino acid sequences were as shown in Table 10.

TABLE 10

| Origin | Peptide | Internal partial amino acid sequence |
| --- | --- | --- |
| Rhizobium sp. M-11 (FERM BP-4130) | RT41 | histidine-glycine-glutamic acid-glycine-asparagine-threonine-tryptophane-glycine-aspartic acid-serine (SEQ ID NO: 3) |
| | RT46 | aspartic acid-glutamic acid-arginine-alanine-valine-histidine-isoleucine-leucine-glutamic acid-glutamic acid (SEQ ID NO: 4) |
| | RT54 | leucine-aspartic acid-tryptophane-alanine-glutamic acid-alanine-serine-alanine-glycine-aspartic acid (SEQ ID NO: 5) |
| Arthrobacter sp. Q36 (FERM BP-4316) | AT30 | glutamine-glycine-glutamic acid-glycine-asparagine-threonine-tryptophane-glycine-aspartic acid-serine (SEQ ID NO: 6) |
| | AT48 | aspartic acid-glutamic acid-arginine-alanine-valine-histidine-isoleucine-leucine-glutamic acid-aspartic acid (SEQ ID NO: 7) |
| | AT7 | leucine-aspartic acid-tryptophane-alanine-glutamic acid-alanine-alanine-glutamic acid-glycine-aspartic acid (SEQ ID NO: 8) |

As evident from Table 10, 9 of 10 amino acid residues in the internal partial amino acid sequence of peptide RT41 of the enzyme derived from Rhizobiumsp. M-11 coincided with those of peptide AT30 of the enzyme derived from Arthrobacter sp. Q36, while those of peptide RT46 coincided with those of peptide AT48 with respect to their 9 of 10 amino acid residues. In the case of peptides RT54 and AT7, they were identical with respect to their 8 of 10 amino acid residues. Accordingly, it is judged that the enzyme derived from microorganisms of the genus Rhizobium and that derived from microorganisms of the genus Arthrobacter have a relatively-high homology with respect to their internal partial amino acid sequences which can be expressed by leucine-asparagine-tryptophane-alanine-glutamic acid-alanine-$X_1$-$X_2$-glycine-aspartic acid (SEQ ID NO: 9) (where "$X_1$" means "serine" or "alanine", and "$X_2$" means "alanine" or "glutamic acid"); aspartic acid-glutamic acid-arginine-alanine-valine-histidine-isoleucine-leucine-glutamic acid-$X_3$ (SEQ ID NO: 10) (where "$X_3$" means "glutamic acid" or "aspartic acid"); and $X_4$-glycine-glutamic acid-glycine-asparagine-threonine-tryptophane-glycine-aspartic-serine (SEQ ID NO: 11) (where "$X_4$" means "histidine" or "glutamine").

The following Examples A illustrate the preparation of the present trehalose-releasing enzyme, trehalose prepared therewith, and saccharide compositions containing the trehalose; and Examples B illustrate compositions containing one or more of these trehalose and saccharide compositions:

EXAMPLE A-1

A seed culture of Rhizobium sp. M-11 (FERM BP-4130) was inoculated in a nutrient culture medium and incubated by a fermenter for about 80 hours in accordance with the method in Experiment 1. After completion of the incubation, the resultant culture was filtered to remove cells with an SF-membrane to obtain an about 18 L filtrate, followed by concentrating the filtrate with a UF-membrane into an about one L enzyme solution containing 17.2 units/ml of a non-reducing saccharide-forming enzyme and 20.8 units/ml of the present trehalose-releasing enzyme.

To 15% suspension of potato starch, d.s.b., was added calcium carbonate to give a final concentration of 0.1%, d.s.b., and the resultant solution was adjusted to pH 6.0, mixed with 0.2% by weight of "TERMAMYL 60L", an α-amylase specimen commercialized by Novo Industri A/S, Copenhagen, Denmark, and subjected to an enzymatic reaction at 95° C. for 15 min. The reaction mixture was autoclaved at a pressure of 2 kg/cm$^2$ for 30 min, cooled to 45° C., admixed with 1,000 units/g starch, d.s.b., of "PULLULANASE (EC 3.2.1.41)", an enzyme specimen commercialized by Hayashibara Biochemical Laboratories, Inc., Okayama, Japan, and 0.2 ml/g starch, d.s.b., of the above enzyme solution, and subjected to an enzymatic reaction for 48 hours. The reaction mixture thus obtained was kept at 95° C. for 10 min, cooled and filtered, and the resultant filtrate was in usual manner decolored with an activated charcoal, desalted and purified with ion-exchangers in H- and OH- form, followed by concentrating the resultant solution to obtain a 60% syrup in a yield of about 92%, d.s.b.

The syrup, which contains 70.2% trehalose, 2.4% glucosyltrehalose, 3.3% maltosyltrehalose, 0.7% glucose, 10.1% maltose, 12.9% maltotriose and 0.4% of maltotetraose and higher oligosaccharides, d.s.b., has a moderate and high-quality sweetness and a relatively-low reducing power, as well as an appropriate viscosity and moisture-retaining ability. Because of these it can be arbitrarily used in food products, cosmetics and pharmaceuticals as a sweetener, taste-improving agent, quality-improving agent, stabilizer, diluent, filler and excipient.

EXAMPLE A-2

A saccharide solution as a feed solution, obtained by the method in Example A-1, was fractionated by using a column packed with "XT-1016 (Na$^+$-form, polymerization degree of 4%)", an alkaline-metal strong-acid cation exchange resin commercialized by Tokyo Organic Chemical Industries Ltd., Tokyo, Japan. The procedure was as follows: The resin was packed in 4-jacketed stainless steel columns having an inner diameter of 5.4 cm, and the columns were cascaded in series to give a total gel-bed depth of 20 m. The columns were heated to give the inner column temperature of 55° C. and fed with 5 v/v % of the saccharide solution against the resin while keeping at the temperature, and fed with 55° C. hot water to fractionate the saccharide solution and to remove concomitant saccharides such as maltose and maltotriose, followed by recovering trehalose-rich fractions. The fractions thus obtained were pooled, purified, concentrated, dried in vacuo and pulverized to obtain a high trehalose content powder in a yield of about 56%, d.s.b.

The content of trehalose in the product is about 97%, d.s.b., and the product has a mild and high-quality sweetness, and, because of these it is arbitrarily used in food products, cosmetics and pharmaceuticals as a sweetener, taste-improving agent, quality-improving agent, stabilizer, excipient and filler.

EXAMPLE A-3

A high trehalose content fraction obtained by the method in Example A-2 was in usual manner decolored with an activated charcoal, desalted with an ion-exchanger, and concentrated into an about 70% solution which was then placed in a crystallizer, admixed with about 2% hydrous crystalline trehalose as a seed crystal, and gradually cooled to obtain a massecuite with a crystallinity of about 45%. The massecuite was sprayed from a nozzle equipped at the top of a drying tower at a high pressure of 150 kg/cm$^2$. In the spraying step, the massecuite was simultaneously ventilated with 85° C. hot air being sent from the top of the drying tower, and the resultant crystalline powder was collected on a metal wire netting conveyer provided on the basement of the drying tower, and gradually moved out of the drying tower while a stream of 45° C. air was passing upwards through the metal wire netting. The resultant crystalline powder was injected in an ageing tower and aged for 10 hours to complete the crystallization and drying, followed by recovering a powdery hydrous crystalline trehalose in a yield of about 90% against the material high trehalose content fraction, d.s.b.

The product is substantially non-hygroscopic and handles easily, and these render it arbitrarily useful in food products, cosmetics and pharmaceuticals as a sweetener, taste-improving agent, quality-improving agent, stabilizer, excipient and filler.

EXAMPLE A-4

A high trehalose content fraction obtained by the method in Example A-2 was purified similarly as in Example A-3, and the resultant was placed in an evaporator, and boiled up in vacuo to obtain a syrup with a moisture content of about 3.0%. The resultant syrup was placed in a crystallizer, admixed with one % anhydrous crystalline trehalose against the dry weight of the syrup, and crystallized at 120° C. for 5 min under stirring conditions, and the resultant mixture was placed in a aluminum plain container and aged at 100° C. for 6 hours to obtain a block.

The resultant block was pulverized by a cutter and dried by a fluidized-bed drying to obtain a powdery anhydrous crystalline trehalose with a moisture content of about 0.3% in a yield of about 85% against the material high trehalose content fraction, d.s.b. The product can be arbitrarily used as a desiccant in food products, cosmetics, pharmaceuticals, and their materials and intermediates, and also can be used as a white powdery sweetener in a variety of compositions such as food products, cosmetics and pharmaceuticals.

EXAMPLE A-5

In accordance with the method in Example A-1, a seed culture of a mutant of Rhizobium sp. M-11 (FERM BP-4130) was inoculated in a nutrient culture medium and incubated by a fermenter for about 70 hours. After completion of the incubation, the resultant cells were membrane filtered with an SF-membrane to recover an about 100 L filtrate which was then concentrated with a UF-membrane to obtain an about 5 L enzyme solution containing about 410 units/ml of a non-reducing saccharide-forming enzyme and about 490 units/ml of a trehalose-releasing enzyme.

Six % suspension of potato starch was gelatinized by heating, adjusted to pH 4.5, heated to 50° C., admixed with 500 units/g starch, d.s.b., of an isoamylase specimen commercialized by Hayashibara Biochemical Laboratories, Inc., Okayama, Japan, and subjected to an enzymatic reaction for 20 hours. The reaction mixture was adjusted to pH 6.5, autoclaved at 120° C. for 10 min, cooled to 95° C., admixed with 0.1% per g starch, d.s.b., of "TERMAMYL 60L", an a-amylase specimen commercialized by Novo Industri A/S Copenhagen Denmark, and subjected to an enzymatic reaction for 15 min. The reaction mixture was autoclaved at 130° C. for 30 min, cooled to 45° C., admixed with 0.01 ml per g starch, d.s.b., of the above-mentioned enzyme solution, and subjected to an enzymatic reaction for 64 hours. The resultant reaction mixture was kept at 95° C. for 10 rain, cooled to 50° C., adjusted to pH 5.0, admixed with 10 units/g starch, d.s.b., of "GLUCOZYME", a glucoamylase specimen commercialized by Nagase Biochemicals, Ltd., Kyoto, Japan, subjected to an enzymatic reaction for 40 hours, and heated to inactivate the remaining enzyme. The solution thus obtained was in usual manner decolored with an activated charcoal, desalted with an ion-exchanger and concentrated into an about 60% solution containing 80.5% trehalose, d.s.b. The solution was concentrated into an about 84% solution which was then placed in a crystallizer and admixed with an about 2% hydrous crystalline trehalose as a seed crystal against the dry weight of the solution to crystallize trehalose under stirring conditions. The resultant was placed in a plain plastic-vessel and allowed to stand at an ambient temperature for 3 days to form a block which was then pulverized by a cutter to obtain a powdery hydrous crystalline trehalose in a yield of about 90% against the material starch, d.s.b.

The product is substantially non-hygroscopic and handles easily, and these render it arbitrarily useful in a variety of compositions such as food products, cosmetics and pharmaceuticals as a sweetener, taste-improving agent, quality-improving agent, stabilizer, excipient and filler.

EXAMPLE A-6

A seed culture of a microorganism of Arthrobacter sp. Q36 (FERM BP-4316) was inoculated in a nutrient culture medium and cultured with a fermenter for about 72 hours in accordance with the method in Experiment 9. The resultant culture was centrifuged at 10,000rpm for 30 min to remove cells, and the resultant supernatant was concentrated with a UF-membrane to obtain one L of an enzyme solution containing 16.3 units/ml of a non-reducing saccharide-forming enzyme and 25.1 units/ml of the present trehalose-releasing enzyme.

One part by weight of potato starch was mixed with 6 parts by weight of water and 0.01 part by weight of "NEO-SPITASE", an α-amylase specimen commercialized by Nagase Biochemicals Ltd., Kyoto, Japan, and the resultant mixture was mixed by stirring, adjusted to pH 6.2 and heated to 85°–90° C. to gelatinize and liquefy the starch. The resultant liquefied starch was autoclaved at 120° C. for 10 min to inactivate the remaining enzyme, cooled to 45° C., admixed with 500 units/g starch of an isoamylase specimen commercialized by Hayashibara Biochemical Laboratories, Inc., Okayama, Japan, and 0.2 ml/g starch of the above enzyme solution, and subjected to an enzymatic reaction for 48 hours. After completion of the reaction, the reaction mixture was heated at 95° C. for 10 min to inactivate the remaining enzyme, adjusted to 50° C. and pH 5.0, admixed with 10 units/g starch "GLUCOZYME", a glucoamylase specimen commercialized by Nagase Biochemicals Ltd., Kyoto, Japan, subjected to an enzymatic reaction for 40 hours, and heated to inactivate the remaining enzyme. The reaction mixture thus obtained was in usual manner decolored with an activated charcoal, desalted with an ion-exchanger, and concentrated into an about 60% solution containing 78.3% trehalose, d.s.b. In accordance with the method in Example A-2 except for using as the ion-exchanger "CG 6000 ($Na^+$-form)", an alkaline-metal strong-acid cation-exchange resin commercialized by Japan Organo Co, Ltd., Tokyo, Japan, the concentrated solution was subjected to an ion-exchange column chromatography to obtain a high trehalose content fraction containing about 95% trehalose, d.s.b. The fraction was concentrated to give a concentration of 75%, placed in a crystallizer, crystallized by the addition of about 2% hydrous crystalline trehalose as a seed crystal under stirring conditions, transferred to a plain plastic-container, allowed to stand and aged at an ambient temperature for 3 days to obtain a block, followed by pulverizing it with a cutter to obtain a powdery hydrous crystalline trehalose in a yield of about 70% against the material starch, d.s.b.

The product, which is substantially free from hygroscopicity and handles easily, can be arbitrarily used as a sweetener, taste-improving agent, quality-improving agent, excipient, filler and diluent in a variety of compositions such as food products, cosmetics and pharmaceuticals.

EXAMPLE A-7

In accordance with the method in Experiment 13, a seed culture of a microorganism of the species *Brevibacterium helvolum* (ATCC 11822) was inoculated in a nutrient culture medium, and cultured by a fermenter for about 72 hours, and the resultant culture was treated with a cell disrupting apparatus. The resultant mixture was centrifuged at 10,000 rpm for 30 min to remove residues, and the resultant supernatant was concentrated with a UF-membrane, followed by the recovery of an about 700 ml solution containing about 8 units/ml of a non-saccharide-forming enzyme and about 12 units/ml of a trehalose-releasing enzyme.

A 33% tapioca starch suspension was admixed with calcium carbonate to give a final concentration of 0.1%, adjusted to pH 6.0, admixed with 0.3% "TERMAMYL 60L", an α-amylase specimen commercialized by Novo Industri A/S, Copenhagen, Denmark, and subjected to an enzymatic reaction at 95° C. for 20 min. The resultant reaction mixture was autoclaved under a pressure of 2 $kg/cm^2$ for 30 min, cooled to 40° C., admixed with 200 units/g starch of an isoamylase specimen commercialized by Hayashibara Biochemical Laboratories, Inc., Okayama, Japan, and 0.2 ml/g starch of the above enzyme solution, and subjected to an enzymatic reaction for 48 hours. The reaction mixture thus obtained was kept at 95° C. for 10 min, cooled and filtered to obtain a filtrate which was then in usual manner decolored with an activated charcoal, desalted with ion-exchangers in H- and OH-form, and concentrated to obtain a 60% syrup in a yield of about 90%, d.s.b.

The product, which contains 60.1% trehalose, 1.4% glucosyltrehalose, 1.5% maltosyltrehalose, 1.0% glucose, 6.5% maltose, 8.3% maltotriose, 21.2% maltotetraose and higher maltooligosaccharides, has a mild and high-quality sweetness as well as a relatively-low reducing power and an adequate moisture-retaining ability. Because of these, it can be used in a variety of compositions such as food products, cosmetics and pharmaceuticals as a sweetener, taste-improving agent, quality-improving agent, stabilizer, excipient, filler and diluent.

EXAMPLE A-8

A high trehalose content solution containing about 95% trehalose, obtained by the method in Example A-6, was in usual manner decolored and desired. The resultant solution was concentrated into an about 75% solution which was then transferred to a crystallizer, admixed with about 2% hydrous crystalline trehalose as a seed crystal, heated to 50° C., gradually cooled to 25° C. while stirring, and subjected to a separation using a basket-type centrifuge. The resultant crystal was washed by spraying it with a small amount of water to obtain a high-purity hydrous crystalline trehalose with a purity of 99% or higher in a yield of about 50%.

EXAMPLE B-1

Sweetener

To one part by weight of a powdery hydrous crystalline trehalose, obtained by the method in Example A-5, was homogeneously added 0.01 part by weight of "αG SWEET", an α-glycosyl stevioside product commercialized by Toyo Sugar Refining Co., Ltd., Tokyo, Japan, and 0.01 part by weight of "ASPARTAME", a product of L-aspartyl-L-phenylalanine methylester commercialized by Ajinomoto Co., Ltd., Tokyo, Japan, and the resultant mixture was fed to a granulator to obtain a granular sweetener. The product has a satisfactory sweetness and an about 2.5-fold higher sweetening power of sucrose, and the caloric value is lowered to about 2/5 of that of sucrose.

Since the product has a satisfactory stability and does not decompose other sweeteners to be mixed, it can be suitably used as a low-caloric sweetener for low-caloric food products for fat persons and diabetics who are restricted to a reduced calorie intake.

The product substantially does not form acids and insoluble glucans when dental carries-inducing microorganisms act on it, and this renders it useful for sweetening food products to prevent dental carries.

EXAMPLE B-2

Hard candy

One hundred parts by weight of 55% sucrose solution was mixed while heating with 30 parts by weight of a trehalose syrup, obtained by the method in Example A-7, and the resultant solution was concentrated in vacuo until the moisture content lowered to below 2%. The concentrated solution was admixed with one part by weight of citric acid and adequate amounts of a lemon flavor and a coloring agent, and the resultant mixture was in usual manner formed into the desired product.

The product is a high-quality hard candy having a satisfactory taste and biting property, as well as having no fear of causing crystallization of sucrose.

EXAMPLE B-3

Chewing gum

Three parts by weight of a gum base was melted by heating until it softened, and the resultant was mixed with 4 parts by weight of sucrose and 3 parts by weight of a hydrous crystalline trehalose powder obtained by the method in Example A-3, and further mixed with adequate amounts of a flavor and a coloring agent. The resultant mixture was in usual manner kneaded by a roll, formed and packed to obtain the desired product.

The product is a chewing gum having a satisfactory texture and taste.

EXAMPLE B-4

Sweetened condensed milk

Three parts by weight of a trehalose syrup obtained by the method in Example A-1 and one part by weight of sucrose were dissolved in 100 parts by weight of fresh milk, and the resultant solution was sterilized by heating with a plate heater, and condensed to give a concentration of 70%, followed by aseptically canning the resultant concentrate into the desired product.

The product has a mild sweetness and a satisfactory taste, and these render it arbitrarily useful as a seasoning for baby foods, foods for infants, fruit, coffee, cocoa and tea.

EXAMPLE B-5

Lactic acid beverage

One hundred and seventy-five parts by weight of defatted milk, 130 parts by weight of a trehalose syrup obtained by the method in Example A-1, and 50 parts by weight of a high lactosucrose content powder as disclosed in Japanese Patent Laid-Open No. 281,795/92 were dissolved in 1,150 parts by weight of water. The resultant solution was sterilized at 65° C. for 30 min, cooled to 40° C. and inoculated with 30 parts by weight of lactic acid bacterium as a starter, followed by the incubation at 37° C. for 8 hours to obtain the desired product.

The product is a lactic acid beverage with a satisfactory taste and flavor. Since the product contains oligosaccharides, it stably retains lactic acid bacteria and promotes the growth of bifid bacteria.

EXAMPLE B-6

Powdered juice

Thirty-three parts by weight of a powdered orange juice prepared by spray drying was mixed to homogeneity with 50 parts by weight of a high trehalose content powder obtained by the method in Example A-2, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan, and an adequate amount of a powdered flavor. The resultant mixture was pulverized and fed to a fluidized-bed granulator to obtain granules while being sprayed with as a binder a trehalose syrup, obtained by the method in Example A-1, and ventilated with 40° C. air. The granules thus obtained were weighed and packed to obtain the desired product.

The product containing 30% orange juice, d.s.b., retained its high quality for a relatively-long period of time without giving an unsatisfactory taste and smell.

EXAMPLE B-7

Custard cream

One hundred parts by weight of corn starch, 100 parts by weight of a trehalose syrup obtained by the method in Example A-7, 80 parts by weight of maltose, 20 parts by weight of sucrose, and one part by weight of salt were mixed to homogeneity. The resultant mixture was admixed with 280 parts by weight of egg, and gradually added with 1,000 parts by weight of a boiling milk. The mixture thus obtained was continued stirring under heating conditions, and the heating was stopped when the corn starch in the mixture was completely gelatinized to give the whole contents semitransparent, followed by cooling the mixture and adding thereto an adequate amount of a vanilla flavor. The resultant mixture was weighed, injected and packed to obtain the desired product.

The product has a smooth surface and gloss, as well as a mild taste and sweetness.

EXAMPLE B-8

Uiro-no-moto (premix of starch paste)

Ninety parts by weight of rice powder, 20 parts by weight of corn starch, 40 parts by weight of sucrose, 80 parts by weight of a powdery hydrous crystalline trehalose obtained by the method in Example A-3, and 4 parts by weight of pullulan were mixed to homogeneity to obtain a uiro-no-moto. The product was kneaded with adequate amounts of matcha (green tea) and water, and the mixture was placed in a container and steamed up for 60 min to obtain a matcha-uiro.

The product has a satisfactory gloss and biting property, as well as a satisfactory flavor and taste, and has a relatively-long shelf-life because the retrogradation of starch is well inhibited.

EXAMPLE B-9

An (beans paste)

Ten parts by weight of adzuki beans as a material was in usual manner mixed with water and boiled, followed by removing the astringency, harshness of the beans, and water-soluble impurities to obtain about 21 parts by weight of "adzuki-tsubu-an". To the resultant were added 14 parts by weight of sucrose, 5 parts by weight of a trehalose syrup obtained by the method in Example A-1, and 4 parts by weight of water, and the resultant mixture was boiled, mixed with a small amount of salad oil, and carefully kneaded up so as not to paste the beans. Thus, the desired product was obtained in a yield of about 35 kg.

The product free from discoloration induced by boiling has a satisfactory taste and flavor, and these render it useful as a material an for bean-jam buns, buns with bean-jam filling, dumplings, bean-jam-filled wafers, sherbets and ice creams.

EXAMPLE B-10

Bread

One hundred parts by weight of wheat powder, 2 parts by weight of yeast, 5 parts by weight of sugar, one part by weight of a powdery hydrous crystalline trehalose obtained by the method in Example A-3, 0.1 part by weight of inorganic yeast food were kneaded with water in usual manner, fermented at 26° C. for 2 hours, aged for 30 min and baked up.

The product is a high-quality bread having a satisfactory hue and rising, as well as a satisfactory elasticity and mild sweetness.

EXAMPLE B-11

Ham

To one thousand parts by weight of sliced ham meat were added and ground to homogeneity 15 parts by weight of salt and 3 parts by weight of potassium nitrate, and the ham meat slices were piled up and allowed to stand overnight in a cold-storage room. Thereafter, the resultant slices were first soaked in a salt solution consisting of 500 parts by weight of water, 100 parts by weight of salt, 3 parts by weight potassium nitrate, 40 parts by weight of a powder containing non-reducing saccharides prepared by the method in Example A-6, and an adequate amount of a peppermint for 7 days in a cold-storage room, then washed with cold water in usual manner, tied up, smoked, cooked, cooled and packed to obtain the desired product.

The product is a high-quality ham having a satisfactory hue, taste and flavor.

EXAMPLE B-12

Powdery peptide containing 40% edible soy beans commercialized by Fuji Oil Co., Ltd., Tokyo, Japan, was mixed with 2 parts by weight of a powder containing a powdery hydrous crystalline trehalose prepared by the method in Example A-6, and the resultant mixture was placed in a plastic vessel, dried in vacuo at 50° C., and pulverized to obtain a powdery peptide.

The product having a satisfactory taste and flavor can be arbitrary used as a material for confectioneries such as premixes, sherbets and ice creams, as well as baby foods and nutritions for therapy in the form of an oral or an intubation feeding.

EXAMPLE B-13

Powdered miso

To one part by weight of akamiso (a kind of miso) was added 3 parts by weight of a powdery anhydrous crystalline trehalose obtained by the method in Example A-4, and the mixture was poured into a metal plate having hemisphere wells on its surface and allowed to stand at an ambient temperature overnight to obtain miso solids, about 4 g weight each, which were then subjected to a pulverizer to obtain the desired product.

The product can be arbitrarily used as a seasoning for instant noodles and soups, as well as a miso confectionery.

EXAMPLE B-14

Powdery egg yolk

Egg yolks prepared from fresh eggs were sterilized at 60°–64° C. by a plate heater, and one part by weight of the resultant liquid was mixed with 4 parts by weight of a powdery anhydrous crystalline trehalose prepared by the method in Example A-4 with respect to one part by weight of the liquid. The resultant mixture was transferred to a vessel, allowed to stand overnight to form a block while the anhydrous crystalline trehalose was allowing to convert into hydrous crystalline trehalose. The block thus obtained was pulverized by a cutter to obtain a powdery egg yolk.

The product can be arbitrarily used as a material for confectioneries for premixes, sherbets, ice creams and emulsifiers, as well as baby foods and nutritions for therapy in the form of an oral or an intubation feeding. The product can be also used as a skin refiner and hair restorer.

EXAMPLE B-15

Cosmetic cream

Two parts by weight of polyoxyethylene glycol monostearate, 5 parts by weight of glyceryl monostearate, self-emulsifying, 2 parts by weight of a high trehalose content powder obtained by the method in Example A-2, one part by weight of α-glycosyl rutin, one part by weight of liquid petrolatum, 10 parts by weight of glyceryl tri-2-ethylhexanoate, and an adequate amount of an antiseptic were in usual manner dissolved by heating. The resultant solution was admixed with 2 parts by weight of L-lactic acid, 5 parts by weight of 1,3-butylene glycol and 66 parts by weight of refined water, and the resultant mixture was emulsified by a homogenizer and admixed with an adequate amount of a flavor under stirring conditions to obtain a cosmetic cream.

The product having a relatively-high stability can be arbitrarily useful as a high-quality sunscreen, skin-refining agent and skin-whitening agent.

EXAMPLE B-16

Powdery ginseng extract

A half part by weight of ginseng extract was mixed with 1.5 parts by weight of a powdery anhydrous crystalline trehalose prepared by the method in Example A-4, and the resultant mixture was transferred to a plain container, allowed to stand for 2 days to convert anhydrous crystalline trehalose into hydrous crystalline trehalose to form a block. The resultant block was pulverized by a cutter and classified to obtain a powdery ginseng extract.

The product and adequate amounts of powdery vitamins B1 and B2 were subjected to a granulator to obtain a powdery ginseng extract containing vitamins.

The product thus obtained can be arbitrarily used as a tonic, fatigue-relieving agent and vitality-imparting agent. The product can be also used as a hair restorer.

EXAMPLE B-17

Solid pharmaceutical

A natural human interferon-α preparation, commercialized by Cosmo Bio, Tokyo, Japan, was in usual manner fed to a column of an immobilized anti-human interferon-α antibody to adsorb the interferon-α, and a buffer containing calf serum albumin as a stabilizer was fed to the column, followed by removing an excessive amount of the albumin. Thereafter, the interferon-α was eluted from the column with a physiological saline containing 5% of a high trehalose content powder, prepared by the method in Example A-2, while the pH of the physiological saline was varying. The resultant eluate was membrane filtered, and the filtrate was dehydrated by the addition of about 20-fold volumes of "FINETOSE®", an anhydrous crystalline maltose powder commercialized by Hayashibara Shoji, Inc., Okayama, Japan, followed by pulverizing the resultant dehydrated product, and tabletting the resultant powder by a tabletting machine to obtain tablets containing about 150 units of the natural human interferon-α per one tablet, about 200 mg weight.

The product can be orally administered as a sublingual tablet to patients at a dose of 1–10 tablets/adult/day, and arbitrarily used to treat viral diseases, allergys, rheumatisms, diabetes and malignant tumors. More particularly, the product can be suitably used as a therapeutic agent for AIDS and hepatitis, the number of patients suffering from these diseases has been remarkably increased. The trehalose and maltose incorporated in the product act as a stabilizer for the natural human interferon-α, so that the activity is well retained for a relatively-long period of time even at an ambient temperature.

EXAMPLE B-18

Sugar coated tablet

A crude tablet as a core, 150 mg weight, was coated with a solution consisting of 40 parts by weight of a powdery hydrous crystalline trehalose obtained by the method in Example A-3, 2 parts by weight of pullulan having an average molecular weight of 200,000, 30 parts by weight of water, 25 parts by weight of talc, and 3 parts by weight of titanium oxide until the total weight reached to about 230 mg, and the resultant was further coated with a solution consisting of 65 parts by weight of a fresh preparation of the same powdery hydrous crystalline trehalose, one part by weight of pullulan, and 34 parts by weight of water, and glossed with a liquid wax to obtain a sugar coated tablet having a satisfactory gloss and appearance.

The product has a relatively-high shock tolerance and retains its high quality for a relatively-long period of time.

EXAMPLE B-19

Dentifrice

A dentifrice was prepared in usual manner by mixing the following ingredients:

| | |
|---|---|
| Calcium monohydrogenphosphate | 45.0% |
| Pullulan | 2.95% |
| Sodium lauryl sulfate | 1.5% |
| Glycerine | 20.0% |
| Polyoxyethylene sorbitan laurate | 0.5% |
| Antiseptic | 0.05% |
| Powdery hydrous crystalline trehalose prepared by the method in Example A-3 | 12.0% |
| Maltitol | 5.0% |
| Water | 13.0% |

The product is satisfactorily used as a dentifrice for infants because it has an adequate sweetness.

EXAMPLE B-20

Solid preparation for intubation feeding

A composition consisting of the following compositions was prepared: Five hundred parts by weight of a powdery hydrous crystalline trehalose prepared by the method in Example A-6, 270 parts by weight of powdered egg yolk, 209 parts by weight of defatted milk, 4.4 parts by weight of sodium chloride, 1.8 parts by weight of potassium chloride, 4 parts by weight of magnesium sulfate, 0.01 part by weight of thiamine, 0.1 part by weight of sodium ascorbate, 0.6 parts by weight of vitamin E acetate, and 0.04 parts by weight of nicotinamide. Twenty-five g aliquots of the composition were injected into moisture-proof laminated small bags and heat sealed to obtain the desired product.

One bag of the product is dissolved in about 150–300 ml of water into a fluid food, and orally or parenterally administered to nasal cavity, stomach or intestine by intubation feeding to supplement energy to living bodies.

EXAMPLE B-21

Hyperalimentation

A high-purity hydrous crystalline trehalose, prepared by the method in Example A-8, was dissolved in water into an about 10 w/v % aqueous trehalose solution which was then in usual manner membrane filtered to remove pyrogen, aseptically injected into a plastic bottle, and sealed to obtain the desired product.

The product, which is a satisfactorily stable hyperalimentation substantially free of change on standing, is suitable for intravenous- and intraperitoneal-administrations. A 10 w/v % solution of the product is isotonic to blood, and this means it can supplement energy to living bodies at 2-fold higher concentration than in the case of glucose.

EXAMPLE B-22

Hyperalimentation

A high-purity hydrous crystalline trehalose, prepared by the method in Example A-8, and an amino acid composition consisting of the following components were dissolved by stirring in water to give respective concentrations of 5 w/v % and 30 w/v %, and, similarly as in Example B-10 the resultant solution was purified to obtain a pyrogen-free solution, followed by injecting it into a plastic bottle and sealed to obtain the desired product.

| Components of amino acid composition | |
| --- | --- |
| Component | mg/100 ml |
| L-Isoleucine | 180 |
| L-Leucine | 410 |
| L-Lysine monohydrochloride | 620 |
| L-Methionine | 240 |
| L-Phenyl alanine | 290 |
| L-Threonine | 180 |
| L-Tryptophane | 60 |
| L-Valine | 200 |
| L-Arginine hydrochloride | 270 |
| L-Histidine monohydrochloride | 130 |
| Glycine | 340 |

Although the product is a multiple hyperalimentation containing trehalose and amino acids, it is satisfactorily stable without substantial change on standing and can be suitably administered intravenously and intraperitoneally to living bodies. The product can be arbitrarily used to supplement energy as well as amino acids to living bodies.

EXAMPLE B-23

Ointment for treating trauma

Two hundred parts by weight of a high trehalose content powder, prepared by the method in Example A-2, and 300 parts by weight of maltose were admixed with 50 parts by weight of methanol solution containing 3 parts by weight of iodine, and the resultant solution was mixed with 200 parts by weight of a 10 w/v % aqueous pullulan solution to obtain the desired product having a satisfactory extensibility and adhesiveness.

The iodine contained in the product exerts a bactericidal activity, and the trehalose in the product acts as an energy-supplementing agent on viable cells, and because of these the product shortens a healing period and satisfactorily heals a wound surface.

As is evident from above, the present novel trehalose-releasing enzyme releases trehalose from non-reducing saccharides having a trehalose structure as an end unit and having a degree of glucose polymerization of 3 or higher, and forms trehalose in a relatively-high yield when allowed to act on reducing partial starch hydrolysates together with a non-reducing saccharide-forming enzyme. The trehalose thus obtained can be readily separated and purified, and the resultant purified trehalose and saccharide compositions containing it has a satisfactory stability as well as a relatively-high quality and mild sweetness. It is readily assimilated, absorbed and utilized by living bodies when orally administered intact or parenterally administered in the form of a transfusion agent. Trehalose per se and saccharide compositions containing the same can be arbitrarily used as a sweetener, taste-improving agent, quality-improving agent, stabilizer, excipient and filler in a variety of compositions such as food products, cosmetics and pharmaceuticals.

Thus, the present invention provides a novel technique to prepare trehalose and saccharide compositions containing the same in an industrial-scale and a relatively-low cost from partial starch hydrolysates prepared from starch, a cheap and abundant natural source. Therefore, the present invention gives an unfathomable great influence on the fields such as starch-, enzyme- and biochemical-sciences, and other industrial fields, especially, food-, cosmetic- and pharmaceutical-industries, as well as forestry, fisheries, and agricultural-, livestock- and chemical-industries. Thus, the influence of the present invention on the fields is unfathomably great.

While there has been described what is at present considered to be the preferred-embodiments of the invention, it will be understood the various modifications may be made therein, and it is intended to cover in the appended claims all such modifications as fall within the true spirits and scope of the invention.

---

We claim:

1. A process for preparing a composition containing trehalose, comprising:
   (a) allowing a non-reducing saccharide-forming enzyme together with a trehalose-releasing enzyme to act on a solution containing one or more reducing partial starch hydrolysates having a degree of glucose polymerization of 3 or higher to form trehalose, said non-reducing saccharide-forming enzyme being capable of forming a non-reducing saccharide having a trehalose structure as an end unit and having a degree of glucose polymerization of 3 or higher, and said trehalose-releasing enzyme being capable of specifically hydrolyzing the linkage between a trehalose moiety and the remaining glycosyl moiety in said non-reducing saccharide;
   (b) recovering the resultant trehalose together with or without other saccharide(s); and
   (c) incorporating the trehalose together with or without other saccharide(s) into a material for composition.

2. The process in accordance with claim 1, wherein the composition is a food product.

3. The process in accordance with claim 1, wherein the composition is a cosmetic composition.

4. The process in accordance with claim 1, wherein the composition is a pharmaceutical composition.

5. The process in accordance with claim 1, wherein said glycosyl moiety consists of one or more glucose residues.

6. The process in accordance with claim 1, wherein said trehalose-releasing enzyme has the following physicochemical properties:
   (1) Action
      Specifically hydrolyzing the linkage between a trehalose moiety and the remaining glycosyl moiety in a non-reducing saccharide having a trehalose structure as an end unit and having a degree of glucose polymerization of 3 or higher;
   (2) Molecular weight
      About 57,000 to 68,000 daltons on sodium dodecyl-sulfate-polyacrylamide gel electrophoresis (SDS-PAGE);
   (3) Isoelectric point (pI)
      About 3.3 to 4.6 on isoelectrophoresis using ampholyte;
   (4) Optimum temperature
      About 35°–45° C. when incubated at pH 7.0 for 30 min;
   (5) Optimum pH
      About 6.0–7.5 when incubated at 40° C. for 30 min;
   (6) Thermal stability
      Stable up to a temperature of about 30°–45° C. when incubated at pH 7.0 for 60 min; and
   (7) pH Stability
      Stable at a pH of about 5.0–10.0 when incubated at 25° C. for 16 hours.

7. The process in accordance with claim 1, wherein said trehalose-releasing enzyme has one or more partial amino acid sequences selected from the group consisting of:
   (1) leucine-aspartic acid-tryptophan-alanine-glutamic acid-alanine-$X_1$-$X_2$-glycine-aspartic acid, where $X_1$ means serine or alanine, and $X_2$ means alanine or glutamic acid (SEQ ID NO: 9);
   (2) aspartic acid-glutamic acid-arginine-alanine-valine-histidine-isoleucine-leucine-glutamic acid-$X_3$, where $X_3$ means glutamic acid or aspartic acid (SEQ ID NO: 10); and
   (3) $X_4$-glycine-glutamic acid-glycine-asparagine-threonine-tryptophan-glycine-aspartic acid-serine, where $X_4$ means histidine (SEQ ID NO: 3) or glutamine (SEQ ID NO: 6).

8. The process in accordance with claim 1, wherein said trehalose-releasing enzyme is derived from a microorganism.

9. The process in accordance with claim 8, wherein said microorganism is a microorganism selected from the group consisting of those of the genera Rhizobium, Arthrobacter, Brevibacterium and Micrococcus.

10. The process in accordance with claim 9, wherein said microorganism of the genus Rhizobiumis Rhizobiumsp. M-11 (FERM BP-4130).

11. The process in accordance with claim 9, wherein said microorganism of the genus Arthrobacter is Arthrobacter sp. Q36 (FERM BP-4316).

12. A method to lower the degree of glucose polymerization of a reducing partial starch hydrolysate without increasing its reducing power, which contains a step of allowing a non-reducing saccharide-forming enzyme together with a trehalose-releasing enzyme to act on a solution containing one or more reducing partial starch hydrolysates having a degree of glucose polymerization of 3 or higher, said non-reducing saccharide-forming enzyme being capable of forming one or more non-reducing saccharides having a trehalose structure as an end unit and having a degree of glucose polymerization of 3 or higher, and said trehalose-releasing enzyme being capable of specifically hydrolyzing the linkage between a trehalose moiety and the remaining glycosyl moiety in said non-reducing saccharide.

13. The method in accordance with claim 12, wherein said glycosyl moiety consists of one or more glucose residues.

14. The method in accordance with claim 12, wherein said trechalose-releasing enzyme has the following physico-chemical properties:

(1) Action
   Specifically hydrolyzing the linkage between a trehalose moiety and the remaining glycosyl moiety in a non-reducing saccharide having a trehalose structure as an end unit and having a degree of glucose polymerization of 3 or higher;

(2) Molecular weight
   About 57,000 to 68,000 daltons on sodium dodecyl-sulfate-polyacrylamide gel electrophoresis (SDS-PAGE);

(3) Isoelectric point (pI)
   About 3.3 to 4.6 on isoelectrophoresis using ampholyte;

(4) Optimum temperature
   About 35°–45° C. when incubated at pH 7.0 for 30 min;

(5) Optimum pH
   About 6.0–7.5 when incubated at 40° C. for 30 min;

(6) Thermal stability
   Stable up to a temperature of about 30°–45° C. when incubated at pH 7.0 for 60 min; and (7) pH Stability
   Stable at a pH of about 5.0–10.0 when incubated at 25° C. for 16 hours.

15. The method in accordance with claim 12, wherein said trehalose-releasing enzyme has one or more partial amino acid sequences selected from the group consisting of:

(1) leucine-aspartic acid-tryptophan-alanine-glutamic acid-alanine-$X_1$-$X_2$-glycine-aspartic acid, where $X_1$ means serine or alanine, and $X_2$ means alanine or glutamic acid (SEQ ID NO: 9);

(2) aspartic acid-glutamic acid-arginine-alanine-valine-histidine-isoleucine-leucine-glutamic acid-$X_3$, where $X_3$ means glutamic acid or aspartic acid SEQ ID NO: 10); and (3) $X_4$-glycine-glutamic acid-glycine-asparagine-threonine-tryptophan-glycine-aspartic acid-serine, where $X_4$ means histidine (SEQ ID NO: 3) or glutamine (SEQ ID NO: 6).

16. The method in accordance with claim 12, wherein said trehalose-releasing enzyme is derived from a microorganism.

17. The method in accordance with claim 16, wherein said microorganism is a microorganism selected from the group consisting of those of the genera Rhizobium, Arthrobacter, Brevibacterium and Micrococcus.

18. The method in accordance with claim 17, wherein said microorganism of the genus Rhizobiumis Rhizobiumsp. M-11 (FERM BP-4130).

19. The method in accordance with claim 17, wherein said microorganism of the genus Arthrobacter is Arthrobacter sp. Q36 (FERM BP-4316).

20. The process of claim 1, wherein said solution containing a non-reducing saccharide having a trehalose structure as an end unit and having a degree of glucose polymerization of 3 or higher is obtained by partially hydrolyzing a solution of amylaceous substance using an amylase either with or without a debranching enzyme.

21. The process of claim 12, wherein said solution containing a non-reducing saccharide having a trehalose structure as an end unit and having a degree of glucose polymerization of 3 or higher is obtained by partially hydrolyzing a solution of amylaceous substance using an amylase either with or without a debranching enzyme.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:1:

Ala Lys Pro Val Gln Gly Ala Gly Arg Phe
1               5                   10

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:2:

Thr Pro Thr Tyr Pro Arg Glu Arg Ala Lys
1               5                   10

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:3:

His Gly Glu Gly Asn Thr Trp Gly Asp Ser
1               5                   10

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:4:

Asp Glu Arg Ala Val His Ile Leu Glu Glu
1               5                   10

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:5:

Leu Asp Trp Ala Glu Ala Ser Ala Gly Asp
1               5                   10

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:6:

Gln Gly Glu Gly Asn Thr Trp Gly Asp Ser
1               5                   10

( 2 ) INFORMATION FOR SEQ ID NO:7:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Asp Glu Arg Ala Val His Ile Leu Glu Asp
1               5                   10

( 2 ) INFORMATION FOR SEQ ID NO:8:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Leu Asp Trp Ala Glu Ala Ala Glu Gly Asp
1               5                   10

( 2 ) INFORMATION FOR SEQ ID NO:9:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 7
( D ) OTHER INFORMATION: /note="Xaa =Serine or Alanine"

( i x ) FEATURE:
( A ) NAME/KEY: Peptide
( B ) LOCATION: 8
( D ) OTHER INFORMATION: /note="Xaa =Alanine or Glutamic
acid"

( x i ) SEQUENCE DESCRIPTION: SEQ ID NO:9:

Leu Asp Trp Ala Glu Ala Xaa Xaa Gly Asp
1               5                   10

( 2 ) INFORMATION FOR SEQ ID NO:10:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 10

(D) OTHER INFORMATION: /note="Xaa =Glutamic acid or Aspartic acid"

(xi) SEQUENCE DESCRIPTION: SEQ ID NO:10:

Asp Glu Arg Ala Val His Ile Leu Glu Xaa
1               5                       10

(2) INFORMATION FOR SEQ ID NO:11:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 1
    (D) OTHER INFORMATION: /note="Xaa =Histidine or Glutamine"

(xi) SEQUENCE DESCRIPTION: SEQ ID NO:11:

Xaa Gly Glu Gly Asn Thr Trp Gly Asp Ser
1               5                       10